US012755826B2

(12) United States Patent
Kuperman et al.

(10) Patent No.: US 12,755,826 B2
(45) **Date of Patent: *Oct. 6, 2026**

(54) SYSTEMS AND METHODS FOR MONITORING AND MANAGING NEUROLOGICAL DISEASES AND CONDITIONS

(71) Applicant: Eysz, Inc., Berkeley, CA (US)

(72) Inventors: Rachel Kuperman, Piedmont, CA (US); Parth Amin, Cary, NC (US); Bikramjit Sarkar, San Diego, CA (US)

(73) Assignee: Eysz, Inc., Berkeley, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/008,334

(22) Filed: Jan. 2, 2025

(65) Prior Publication Data

US 2026/0120838 A1 Apr. 30, 2026

Related U.S. Application Data

(63) Continuation of application No. 17/643,363, filed on Dec. 8, 2021, now Pat. No. 12,224,049.

(Continued)

(51) Int. Cl.
*G16H 20/10* (2018.01)
*G16H 40/63* (2018.01)

(52) U.S. Cl.
CPC ............ *G16H 20/10* (2018.01); *G16H 40/63* (2018.01)

(58) Field of Classification Search
CPC ............................... G16H 20/10; G16H 40/63
See application file for complete search history.

(56) References Cited

U.S. PATENT DOCUMENTS 6,315,740 B1 11/2001 Singh
7,643,655 B2 1/2010 Liang et al.
(Continued)

FOREIGN PATENT DOCUMENTS

AU 2021102414 A4 7/2021
EP 3761849 A4 3/2022
(Continued)

OTHER PUBLICATIONS

Lunn J, Donovan T, Litchfield D, Lewis C, Davies R, Crawford T. Saccadic Eye Movement Abnormalities in Children with Epilepsy. PLoS One. Aug. 2, 2016;11(8):e0160508. doi: 10.1371/journal.pone.0160508. PMID: 27483011; PMCID: PMC4970731. (Year: 2016).*

(Continued)

*Primary Examiner* — Joshua B Blanchette

(74) *Attorney, Agent, or Firm* — Fortem IP LLP

(57) ABSTRACT

Systems and methods for monitoring and managing neurological diseases and conditions are disclosed herein. In some embodiments, a method for monitoring a patient having a neurological disease or condition includes receiving, from one or more patient monitoring devices, first patient data for a baseline time period. The method can include determining, based on the first patient data, first seizure data and first side effect data during the baseline time period. The method can further include receiving, from the one or more patient monitoring devices, second patient data for a treatment time period, and determining, based on the second patient data, (Continued)

second seizure data and second side effect data during the treatment time period. The method can also include generating a personalized dose-response profile for the patient based on the first and second seizure data and the first and second side effect data.

20 Claims, 16 Drawing Sheets

Related U.S. Application Data

(60) Provisional application No. 63/123,402, filed on Dec. 9, 2020.

(56) References Cited

U.S. PATENT DOCUMENTS

| | | | |
|---|---|---|---|
| 8,852,100 | B2 | 10/2014 | Osorio |
| 8,868,172 | B2 | 10/2014 | Leyde et al. |
| 9,460,400 | B2 | 10/2016 | De Bruin et al. |
| 9,655,515 | B2 | 5/2017 | Schroeder et al. |
| 10,039,445 | B1 | 8/2018 | Torch |
| 10,172,550 | B2 | 1/2019 | Osorio |
| 10,685,748 | B1 | 6/2020 | Chappell et al. |
| 2002/0010352 | A1 | 1/2002 | Llatas et al. |
| 2002/0103512 | A1 | 8/2002 | Echauz et al. |
| 2004/0234103 | A1 | 11/2004 | Steffein |
| 2004/0267152 | A1 | 12/2004 | Pineda |
| 2006/0190419 | A1 | 8/2006 | Bunn et al. |
| 2008/0208072 | A1 | 8/2008 | Fadem et al. |
| 2009/0005860 | A1 | 1/2009 | Gale et al. |
| 2009/0058660 | A1 | 3/2009 | Torch |
| 2011/0257517 | A1 | 10/2011 | Guttag et al. |
| 2011/0263946 | A1 | 10/2011 | El et al. |
| 2012/0008370 | A1 | 1/2012 | Yasuda et al. |
| 2012/0083700 | A1 | 4/2012 | Osorio |
| 2012/0101401 | A1 | 4/2012 | Faul et al. |
| 2014/0275840 | A1 | 9/2014 | Osorio |
| 2015/0126845 | A1 | 5/2015 | Jin et al. |
| 2015/0223731 | A1* | 8/2015 | Sahin ........................ A61B 5/16 600/595 |
| 2015/0227702 | A1 | 8/2015 | Krishna et al. |
| 2016/0022136 | A1 | 1/2016 | Ettenhofer et al. |
| 2017/0049395 | A1 | 2/2017 | Cao |
| 2017/0150930 | A1 | 6/2017 | Shikii et al. |
| 2017/0164893 | A1 | 6/2017 | Narayan et al. |
| 2017/0188895 | A1 | 7/2017 | Nathan |
| 2017/0196497 | A1 | 7/2017 | Ray et al. |
| 2017/0258390 | A1 | 9/2017 | Howard |
| 2017/0347878 | A1 | 12/2017 | Milea et al. |
| 2018/0012090 | A1 | 1/2018 | Herbst |
| 2018/0088669 | A1 | 3/2018 | Ramaprakash et al. |
| 2018/0125404 | A1 | 5/2018 | Bott et al. |
| 2018/0184002 | A1 | 6/2018 | Thukral et al. |
| 2018/0247119 | A1 | 8/2018 | Ryan et al. |
| 2018/0289285 | A1 | 10/2018 | Vardas et al. |
| 2019/0019581 | A1 | 1/2019 | Vaughan et al. |
| 2019/0076657 | A1* | 3/2019 | Stubbs ............... A61N 1/36139 |
| 2019/0254580 | A1 | 8/2019 | Bonneh et al. |
| 2019/0328262 | A1 | 10/2019 | Osorio |
| 2020/0085369 | A1 | 3/2020 | Vu et al. |
| 2020/0187845 | A1 | 6/2020 | Nathan et al. |
| 2021/0000341 | A1 | 1/2021 | Kuperman |
| 2021/0319872 | A1 | 10/2021 | Valentine |
| 2022/0022805 | A1 | 1/2022 | Kuperman et al. |
| 2022/0180993 | A1 | 6/2022 | Kuperman et al. |
| 2023/0062081 | A1 | 3/2023 | Kuperman et al. |

FOREIGN PATENT DOCUMENTS

| | | | |
|---|---|---|---|
| GB | 2571265 | A | 8/2019 |
| IN | 202041027872 | A | 8/2020 |
| JP | 2017100039 | A | 6/2017 |
| KR | 20120053389 | A | 5/2012 |
| WO | 2010015029 | A1 | 2/2010 |
| WO | 2017087680 | A1 | 5/2017 |
| WO | 2019013456 | A1 | 1/2019 |
| WO | 2019173106 | A1 | 9/2019 |
| WO | 2019207510 | A1 | 10/2019 |
| WO | 2022020433 | A9 | 1/2022 |
| WO | 2022126114 | A1 | 6/2022 |
| WO | 2023034816 | A1 | 3/2023 |

OTHER PUBLICATIONS

"Soldier Mounted Eye Com 7 & 8 Eye Monitoring Biosensor, Communicator & Controller", SBIR.gov, 4 pages, https://www.sbir.gov/sbirsearch/detail/349032; accessed May 13, 2020.

An, Na, Decline of Dosage Regimen Patents in Light of Emerging Next-Generation DNA Sequencing Technology and Possible Strategic Responses, 17 Minn. J.L. Sci. & Tech. 907 (2016).

Coelho et al., "Electrooculogram and Submandibular Montage to Distinguish Different Eye, Eyelid, and Tonge Movements in Electroencephalographic Studies", Clinical Neurophysiology, 129(11), pp. 2380-2391 (2018).

Dinges, David F. et al., Final Report: Evaluation of Techniques for Ocular Measurement as an Index of Fatigue and as the Basis for Alertness Management, U.S. Department of Transportation, Report No. 808 762, Apr. 1998, 116 pages.

Eckstein, Maria K. et al., Beyond eye gaze: What else can eyetracking reveal about cognition and cognitive development?, Development Cognitive Neuroscience 25 (2017) 69-71.

Fishman, Jesse et al, Antiepileptic Drug Titration and Related Health Care Resource Use and Costs, Journal of Managed Care & Specialty Pharmacy, 2018; 24(9):929-38.

Kessler, Suha Kilaru, Pretreatment seizure semiology in childhood absence epilepsy, American Academy of Neurology, 89, 2017, 673-679.

Lee et al., Automated epileptic seizure waveform detection method based on the feature of the mean slope of wavelet coefficient counts using a hidden Markov model and EEG signals, ETRI Journal, 42(2):217-229 (2020).

Lempert, Thomas et al., The eye movements of syncope, American Academy og Neurology, 1996; 46: 1086-1088.

Luke, Steven G. et al., Predicting eye-movement characteristics across multiple tasks from working memory and executive control, Memory & Cognition, (2018), 46: 826-839.

Panayiotopoulos, C.P., Typical absence seizures and their treatment, Arch Dis Child, 1999; 81: 351-355.

Perucca, Emilio et al., Overtreatment in Epilepsy How It Occurs and How It Can Be Avoided, CNS Drugs, 2005, 19 (11): 897-908.

Rayner, Keith, Eye Movements in Reading and Information Processing: 20 Years of Research, Psychological Bulletin, 1998, vol. 124, No. 3, 372-422.

Reilly, James L., Pharmacological treatment effects on eye movement control, Brain Cognition, Dec. 2008; 68 (3): 415-435.

Richardson, Elizabeth J. et al., Structural and functional neuroimaging correlates of depression in temporal lobe epilepsy, Epilepsy & Behavior, 10 (2007), 242-249.

St. Louis, EK, Minimizing AED Adverse Effects: Improving Quality of Life in the Interictal State in Epilepsy Care, Current Neuropharmacology, 2009, 7, 106-114.

Van De Val, et al., Non-EEG Seizure Detection Systems and Potential SUDEP Prevention: State of the Art, Seizure 41,141-153 (2016).

Van Dijkman et al., Pharmacotherapy in pediatric epilepsy: from trial and error to rational drug and dose selection—a long way to go, Expert Opinion on Drug Metabolism & Toxicology, 12:10, 1143-1156, 2016.

"Epihunter Absence: Phase 3, prospective, multicenter validation study", retrieved from URL: https://www.epihunter.com/hubfs/Epihunter%20Absence%20Phase%203%2C%20prospective%2C%20multicenter%20validation%20study.pdf, 2 Pages.

Adams, et al., "Hyperventilation and 6-hour EEG recording in evaluation of absence seizures", Neurology, vol. 31, Sep. 1981, pp. 1175-1177.

(56) References Cited

OTHER PUBLICATIONS

Afifi, et al., "Seizure-Induced Miosis and Ptosis: Association with Temporal Lobe Magnetic Resonance Imaging Abnormalities", Journal Child Neurol, 5(2); pp. 142-146.
Akman, et al., "Seizure Frequency in Children with Epilepsy: Factors Influencing Accuracy and Parental Awareness", Seizure; 18(7); pp. 524-529, 2009.
Bauder, et al., "Neonatal Seizures: Eyes Open or Closed?", Epilepsia, 48(2); pp. 394-396.
Centeno, et al., "Epilepsy causing pupillary hippus: an unusual semiology", Epilepsia, 52(8); pp. e93-e96.
Chua, KC , et al., "Application of higher order statistics/spectra in biomedical signals—A review", Medical Eng. Phys, 32 (7); pp. 679-689, Sep. 2010. doi: 10.1016/j.medengphy.2010.04.009. Epub May 13, 2010. PMID: 20466580. (Year: 2010).
Chung, et al., "Ictal eye closure is a reliable indicator for psychogenic nonepileptic seizures", Neurology; 66; pp. 1730-1731.
Detoledo, et al., "Patterns of involvement of facial muscles during epileptic and nonepileptic events: Review of 654 events", Neurology, 47; pp. 621-625.
Devinsky, "Effects of Seizures on Autonomic and Cardiovascular Function", Epilepsy Curr, 4(2); pp. 43-46, 2004.
Elmali, et al., "Evaluation of absences and myoclonic seizures in adults with genetic (idiopathic) generalized epilepsy: a comparison between self-evaluation and objective evaluation based on home video-EEG telemetry", Epileptic Disord, vol. 23, No. 5, Oct. 1, 2021, pp. 719-732.
Eyeware, "Head & Eye Tracker Software", AI-powered head and eye tracking software that supercharges webcams and 3D sensors, 9 Pages.
Fujisaka, et al., "Stability Theory of Synchronized Motion in Coupled-Oscillator Systems", Progr Theoret Phys, 69; pp. 32-47, 1983.
Hoppe, et al., "Accuracy of Patient Seizure Counts", Arch Neurol, 64(11); pp. 1595-1599, 2007.
Hunter, "epihunter Video", retrieved from URL: https://www.epihunter.com/en/epihunter-video?hsLang=en-us, Aug. 12, 2022, 4 Pages.
Kane, et al., "Hyperventilation during electroencephalography: Safety and efficacy", Seizure 23 (2014) 129-134.
Kaplan, "Gaze Deviation from Contralateral Pseudoperiodic Lateralized Epileptiform Discharges (PLEDs)", Epilepsia, 46(6); pp. 977-979.
Kaplan, et al., "Neurophysiologic and clinical correlations of epileptic nystagmus", Neurology, 43(12); pp. 2508-2514, P.
Kaplan, et al., "Vertical and horizontal epileptic gaze deviation and nystagmus", Neurology, 39(10); pp. 1391-1393.
Kessler, et al., "A Practical Guide to Treatment of Childhood Absence Epilepsy", Pediatric Drugs, (2019) 21:15-24.
Korff, et al., "Paroxysmal Events in Infants: Persistent Eye Closure Makes Seizures Unlikely", Pediatrics, 11; pp. e485-e486.
Lal, "Non-EEG Physiological Signal Based Seizure Monitoring System", Embrace (K172935), Dec. 27, 2017, 8 Pages.
Lee, et al., "Epileptic nystagmus: A case report and systematic review", Epilepsy Behav Case Rep, 18(2); pp. 156-160.
Lunn, et al., Saccadic Eye Movement Abnormalities in Children with Epilepsy, PLOS ONE, 11(8), 2016, 14 pages.
Malone, et al., "Interobserver Agreement in Neonatal Seizure Identification", Epilepsia 50(9); pp. 2097-2101.(2009).
Meier, et al., "Detecting Epileptic Seizures in Long-Term Human EEG: A New Approach to Automatic Online and Real-Time Detection and Classification of Polymorphic Seizure PatternH", J Clin Neurophysiol., 25(3); pp. 119-131. (2008).
Mendel, "Tutorial on Higher-Order Statistics (Spectra) in Signal Processing and System Theory: Theoretical Results and Some Applications", IEEE, 79(3); pp. 278-305. (1991).
Orren, et al., "Relation Between Ocular Manifestations and Onset of Spike-and-Wave Discharges in Petit Mal Epilepsy", Epilpesia, 16; pp. 771-779.
Pasley, et al., "Reconstructing Speech from Human Auditory Cortex", PLoS Biol 10(1): el001251. (2012).
Rafal, et al., "Seizures triggered by blinking in a non-photosensitive epileptic", Journal of Neurology, Neurosurgery, and Psychiatry, vol. 49, 1986, pp. 445-447.
Rosenblum, et al., "Phase Synchronization of Chaotic Oscillators", Phys Rev Lett, 76; pp. 1804-1807.(1996).
Rozenblat, et al., "Absence seizure provocation during routine EEG: Does position of the child during hyperventilation affect the diagnostic yield", Seizure: European Journal of Epilepsy 79 (2020) 86-89.
Salvati, "Out of thin air: Hyperventilation-triggered seizures", Brain Res. Jan. 15, 2019; 1703: 41-52.
Scaramelli, et al., "Prodromal Symptoms in Epileptic Patients: Clinical Characterization of the Pre-Ictal Phase", Seizure 18(4); pp. 246-250.(2009).
Seizure Tracker LLC , "Seizure Tracker™—Record and share videos of seizures with your care providers", retrieved from URL: https://seizuretracker.com, 3 Pages.
Stafstrom, et al., "Diagnosing and managing childhood absence epilepsy by telemedicine", Epilepsy & Behavior, 2020, 3 Pages.
Stolz, et al., "Epileptic Nystagmus", Epilepsia, vol. 32, No. 6, 1991, pp. 910-918.
Thomson, Kyle E., et al., "Evaluation of subchronic administration of antiseizure drugs in spontaneously seizing rats.", Metcalf CS, Newell TG, Huff J, Edwards SF, West PJ, Wilcox KS; Epilepsia. Jun. 2020;61(6):1301-1311. doi: 10.1111/epi.16531. Epub May 18, 2020. PM ID: 32420627; PMCID: PMC7383749. (Year: 2020).
Thurston, et al., "Epileptic gaze deviation and nystagmus", Neurology, vol. 35, No. 10, Oct. 1985, pp. 1518-1521.
Tusa, et al., "Ipsiversive eye deviation and epileptic nystagmus", Neurology, vol. 40, No. 4, Apr. 1990, pp. 662-665.
Umoove, "Software only Face and Eye Tracking on mobile devices", The Technology, URL: umoove.me/technology.html, retrieved on Aug. 18, 2022, 3 Pages.
Watanabe, et al., "Epileptic Nystagmus Associated with Typical Absence Seizures", Epilepsia, vol. 25, No. 1, 1984, pp. 22-24.
Watemberg, et al., "Adding Video Recording Increases the Diagnostic Yield of Routine Electroencephalograms in Children with Frequent Paroxysmal Events", Epilepsia, vol. 46, No. 5, 2005, pp. 716-719.

* cited by examiner

SYSTEMS AND METHODS FOR MONITORING AND MANAGING NEUROLOGICAL DISEASES AND CONDITIONS

CROSS-REFERENCE TO RELATED APPLICATION(S)

This application is a continuation of U.S. patent application Ser. No. 17/643,363, filed Dec. 8, 2021, now issued as U.S. Pat. No. 12,224,049, which claims the benefit of priority to U.S. Provisional Application No. 63/123,402, filed Dec. 9, 2020, which are incorporated by reference herein in their entirety.

TECHNICAL FIELD

The present technology generally relates to personalized healthcare, and in particular, to systems and methods for monitoring and managing neurological diseases and conditions.

BACKGROUND

Epilepsy is a neurological condition characterized by recurrent seizures. It is one of the oldest recorded diseases in the world, dating back several thousand years. The goal of epilepsy treatment is to stop or reduce seizures with minimal side effects as quickly as possible. Access to reliable seizure data is fundamental to providing optimal epilepsy care from diagnosis to treatment. However, more than 99% of seizures occur outside of clinical settings. Patient self-reporting is the gold standard for measuring seizure data outside of the hospital, but studies have shown that self-reporting data is typically less than 50% accurate. Additionally, neurocognitive effects associated with epilepsy can be subjective and are frequently difficult to measure.

The reliance on poor data contributes to the following challenges in epilepsy diagnosis and management: (1) it typically takes up to 7 years to make a diagnosis of epilepsy, (2) the misdiagnosis rate can be as high as 30%, (3) there is minimal data to help clinicians decide which drug (out of more than 20 currently available medications) to use for initial treatment, (4) the conventional trial and error approach in choosing the type and dosage of medication may result in overdosing (e.g., excess side effects) or underdosing (e.g., ongoing seizure activity), (5) the use of additional tests to supplement the poor data during the treatment cycle may be costly and ineffective, and (6) it takes on average 18 years to refer a patient with refractory epilepsy to an epilepsy center to be evaluated for epilepsy surgery, which may have a much higher success rate for seizure freedom in medication refractory patients than medications alone. Accordingly, improved systems and methods for monitoring and managing epilepsy and other neurological diseases and conditions are needed.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

DETAILED DESCRIPTION

I. Overview of Technology

Figure 1A:
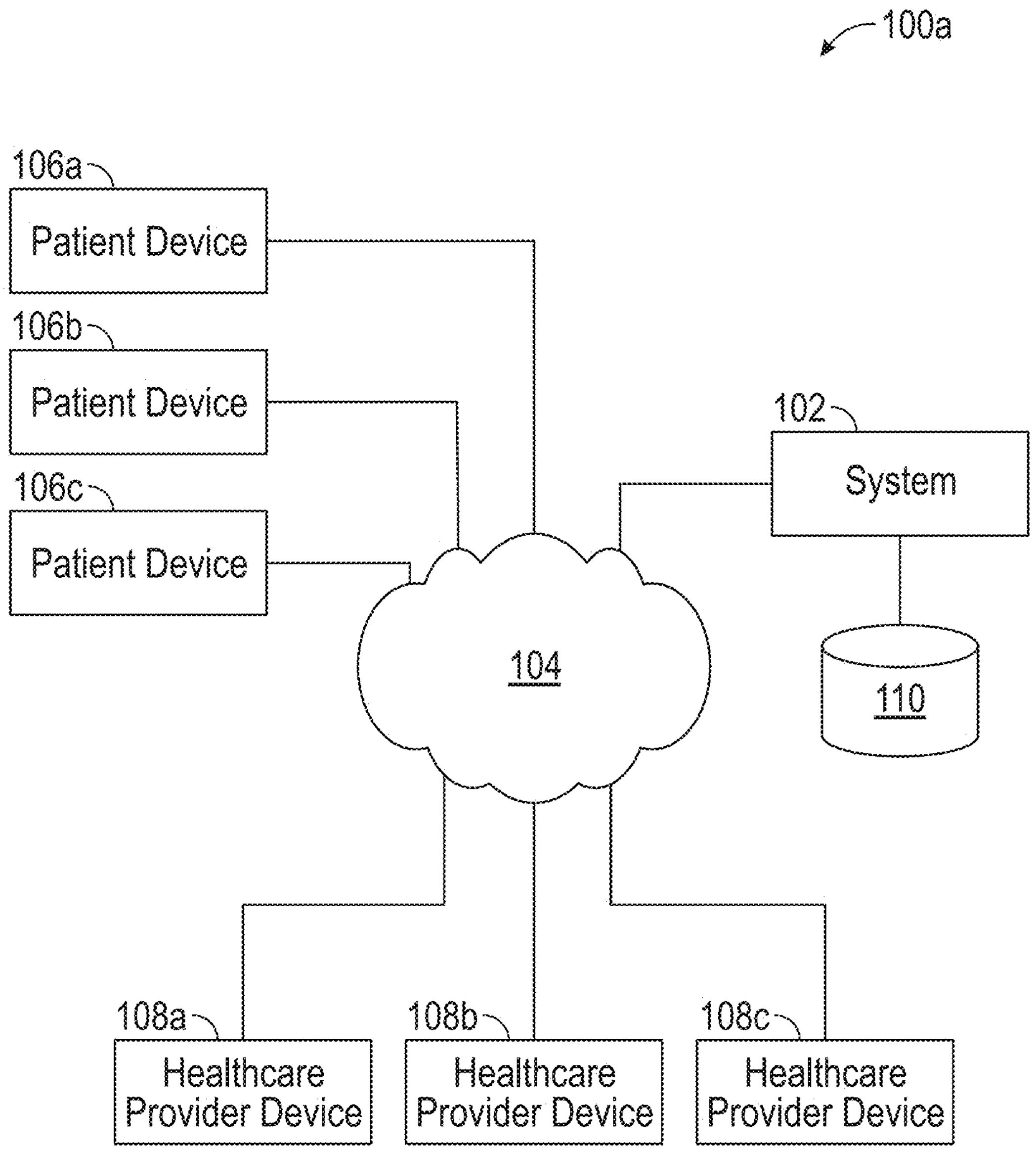
FIG. 1A is a schematic diagram of a computing environment in which a system for monitoring and managing neurological disease and conditions can operate, in accordance with embodiments of the present technology.

The present technology relates to systems and methods for monitoring and managing neurological diseases and conditions, such as epilepsy. In some embodiments, for example, a method for monitoring a patient having a neurological disease or condition includes receiving patient data from at least one patient monitoring device, such as an eye tracking device, a facial tracking device, and/or other suitable device types. The patient data can include baseline data received during a baseline time period (e.g., a period in which the patient has not yet undergone treatment for the neurological disease or condition), and treatment data received during one or more treatment time periods (e.g., periods in which the patient is receiving different dosages of medication). The method can include determining seizure data and/or side effect data over the various time periods. For example, the seizure data can indicate the number, frequency, severity, etc., of seizure events that occur during each time period, while the side effect data can indicate the frequency, severity, types, etc., of adverse neurocognitive effects and/or other functional impairment experienced by the patient during each time period. In some embodiments, the seizure data and/or side effect data are determined from eye movement data and/or other patient data using statistical analysis, pattern recognition, machine learning algorithms, or suitable combinations thereof. Subsequently, the seizure data and side effect data can be used to generate a personalized dose-response profile that shows how the seizure burden and side effects experienced by the patient are affected by treatment (e.g., increasing dosages of medication). In some embodiments, the personalized dose-response profile is used to provide treatment recommendations for more effectively managing the patient's disease or condition, while avoiding or reducing the severity of side effects.

The present technology can provide many advantages over conventional systems, methods, and devices for epilepsy management. For example, conventional approaches may rely upon patient self-reporting data for determining seizure occurrences and/or monitoring side effects (e.g., drowsiness, cognitive slowing) outside of healthcare settings. However, such self-reporting data is frequently inaccurate—patients may underreport or overreport seizures, assessing neurocognitive side effects can be difficult and subjective, etc.—which can make it challenging for the physician to prescribe an effective treatment regimen for the patient. Specifically, physicians typically try to achieve the optimal medication dose quickly to accelerate time to seizure freedom, but reliance on self-reporting data can result in overdosing and/or underdosing of medications. This can contribute to poor quality of life for patients suffering from epilepsy, e.g., excess side effects from overdosing can lead to poor treatment adherence and ongoing seizures, thus resulting in increased healthcare utilization. As many as 30% of epilepsy patients are caught in this cycle of ineffective treatment for years. In the U.S. alone, direct costs related to epilepsy have more than doubled in a decade to $28 billion, while outcomes have not improved in more than 30 years.

Wearable devices based on a variety of technologies have been developed and commercialized to collect seizure data outside of healthcare settings, but frequently come with significant limitations and are typically unable to measure treatment efficacy and quantify side effects to assess therapeutic interventions. For example, conventional electroencephalographic (EEG)-based wearables may have relatively poor sensitivity and may not be capable of differentiating clinical seizures from subclinical seizures. As another example, electromyography (EMG) and accelerometer (ACM)-based devices can typically only detect motor seizures, which are less than 25% of all seizures. Neither of the preceding example device types are typically capable of assessing neurocognitive effects.

To overcome these and other challenges, the present technology provides a system that incorporates the analysis of eye movement data and/or other data (e.g., facial movement data, clinical data such as medication dosage) to produce a dose-response output that allows for personalized treatment recommendations for neurological diseases or conditions such as epilepsy. In some embodiments, the system collects the data, and identifies patterns associated with and/or changes in treatment toxicity (e.g., drowsiness, cognition, mood, vision) and treatment efficacy (e.g., seizure burden). This data can be quantified and used as input to produce a dose-response output for the patient. Accordingly, patient responses, such as increased or reduced efficacy and/or toxicity, can be better understood and correlated with increases or decreases in medications or other treatment modalities over time.

For example, in some embodiments, the systems described herein are configured to perform some or all of the following functions:

1. Collecting and aggregating patient monitoring data, such as (a) eye-movement data (e.g., blink speed, blink frequency, pupil size, eyelid movements, relative eye movement, eye position, gaze angle) from an eye tracking device; (b) video data of the face and/or eyes; (c) brain monitoring data from an electronic device such as EEG data; (d) other data from a sensor or combination of sensors that measures eye movements, facial movements, and/or other relevant patient data (e.g., LIDAR, EEG, video data of the patient's face and/or eyes with EEG); (e) relevant patient self-reporting data (e.g., from electronic seizure diaries, surveys, questionnaires); (f) relevant neuropsychological assessment data (e.g., from electronic performance-based neuropsychological assessments); and/or (g) relevant treatment plan data (e.g., medication dosage, neurostimulation dosage, ketogenic diet ratio) from an external system or device (e.g., electronic health records) and/or from user input.
2. Analyzing the collected, aggregated data to identify patterns associated with and/or changes in neurocognitive effects (e.g., drowsiness, consciousness, cognition, mood, vision) and to quantify seizure burden, therapeutic efficacy, and/or side effects.
3. Producing electronic data to be exported to an external system or device for visualization and/or further processing. The data can be used as a neurological baseline and/or natural history to aid in the diagnosis and treatment of patients with epilepsy.

For individuals with newly diagnosed epilepsy or who are suspected of having epilepsy, the present technology can be used to determine a neurological baseline by analyzing patient data (e.g., eye movement data, facial movement data, questionnaires, EEG) prior to initiation of prophylactic anticonvulsants, other therapeutic regimens such as ketogenic diet, and/or treatment with devices such as vagal nerve stimulators (VNS) or other implantable and/or neurostimulating devices. Specifically, by identifying patterns associated with drowsiness, consciousness, and/or cognition (such as mental processing speed, attention, mood, and/or vision), the present technology can assist neurologists by providing a more accurate phenotype of a person's epilepsy and/or determining an initial therapeutic intervention using the baseline data. For example, determining the patient's baseline phenotype can be useful in epilepsy classification (e.g., very frequent seizures with short durations would fit the phenotype for absence epilepsy) and/or assisting the physician in choosing an appropriate therapy. Similarly, determining baseline information about the patient's cognition can be helpful in avoiding medications or other therapeutics which may exacerbate baseline cognitive challenges. Baseline measurements of cognition can be used to identify phenotypes associated with epileptic encephalopathies, such as Rett syndrome, or cortical blindness associated with genetic disorders or structural brain malformations.

Therapeutic efficacy can be measured as a change in a particular element phenotype, such as the duration and/or severity of seizure and/or postictal depression. Other metrics of therapeutic efficacy, such as tachyphylaxis (a rapid decrease in response to repeated doses over a short time period) and/or tolerance (larger doses required to produce the same effect) can also be measured. Side effects, such as changes in drowsiness, attention, processing speed, etc., can be measured as a change in baseline as it relates to therapeutic changes, and also possibly time from a therapeutic change. In some situations, side effects are known to change over time even when the therapeutic dose is stable. For example, drowsiness may improve over time as the body adjusts to a new therapeutic dose. An individual patient's disease natural history, including early response to treatment, seizure clustering, poor or delayed response to first adequate drug therapy, surrogates of seizure threshold and cognitive functioning), history of a high number of seizures at the time of diagnosis, etc., can be calculated based on a combination of efficacy, therapeutic changes, tolerance/tachyphylaxis, and/or toxicity over time.

Over time, some measures of efficacy may become measures of toxicity, or vice-versa. For example, with some therapeutics, higher doses of therapeutics or polypharmacy may lead to worsening seizure frequency, which can be an example of toxicity. Similarly, attention and reading speed may worsen initially as a therapy is titrated up, but then improve over time as seizure control is obtained, thus moving from a measure of toxicity to a measure of efficacy.

Seizure variability across a given patient can be complicated to understand. For example, a patient may appear to have an improvement in seizure counts after a medication change is made, but in reality, the improvement may instead be attributed to the natural variability of their seizure counts. By establishing a baseline which may require multiple measurements, the present technology can also calculate intrapersonal seizure count variability and/or seizure cycles (e.g., periods when seizures are more frequent or seizure threshold is relatively lower), which can be used to factor into efficacy calculations.

Cognition over time for a given patient can also be complicated to understand. For example, as children with neurologic disease are developing, certain milestones may be reached, missed, or even lost based on the underlying etiology of their disorder and/or response to treatment. Cognition is typically anticipated to change over time both as a function of the natural history of disease and treatment. As the patient ages, cognitive function may evolve, and a new baseline may be reached. As treatment interventions are made, the patterns of drowsiness, consciousness, cognition, mood, and/or vision may change as they relate to the efficacy and/or toxicity of the intervention. By quantifying the changes in efficacy and/or toxicity as treatment interventions are made, a personalized dose-response output can be generated for a patient taking medications and/or undergoing other treatment such as neurostimulation. This allows neurologists to optimize dosing for medications and/or other treatments using such objective data. For example, the systems described herein can produce a graph that compares efficacy to side effects to determine the optimal dosing to maximize efficacy and/or minimize side effects. If the system is unable to obtain reasonable efficacy and/or side effects in the medication dosing range, then pattern recognition, machine learning, and/or similar artificial intelligence techniques can generate an alert informing the physician of poor medication/therapeutic response. Conventionally, these measurements are based on subjective data and are thus near-impossible to track over time in a clinical setting. This can be even more challenging in patients who are refractory to medications, patients on polypharmacy, and younger or older patients. Similarly, patients having epilepsy and severe neurological disorders (e.g., non-verbal patients) may be unable to report even subjective data.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

The headings provided herein are for convenience only and do not interpret the scope or meaning of the claimed present technology. Embodiments under any one heading may be used in conjunction with embodiments under any other heading.

Figure 1B:
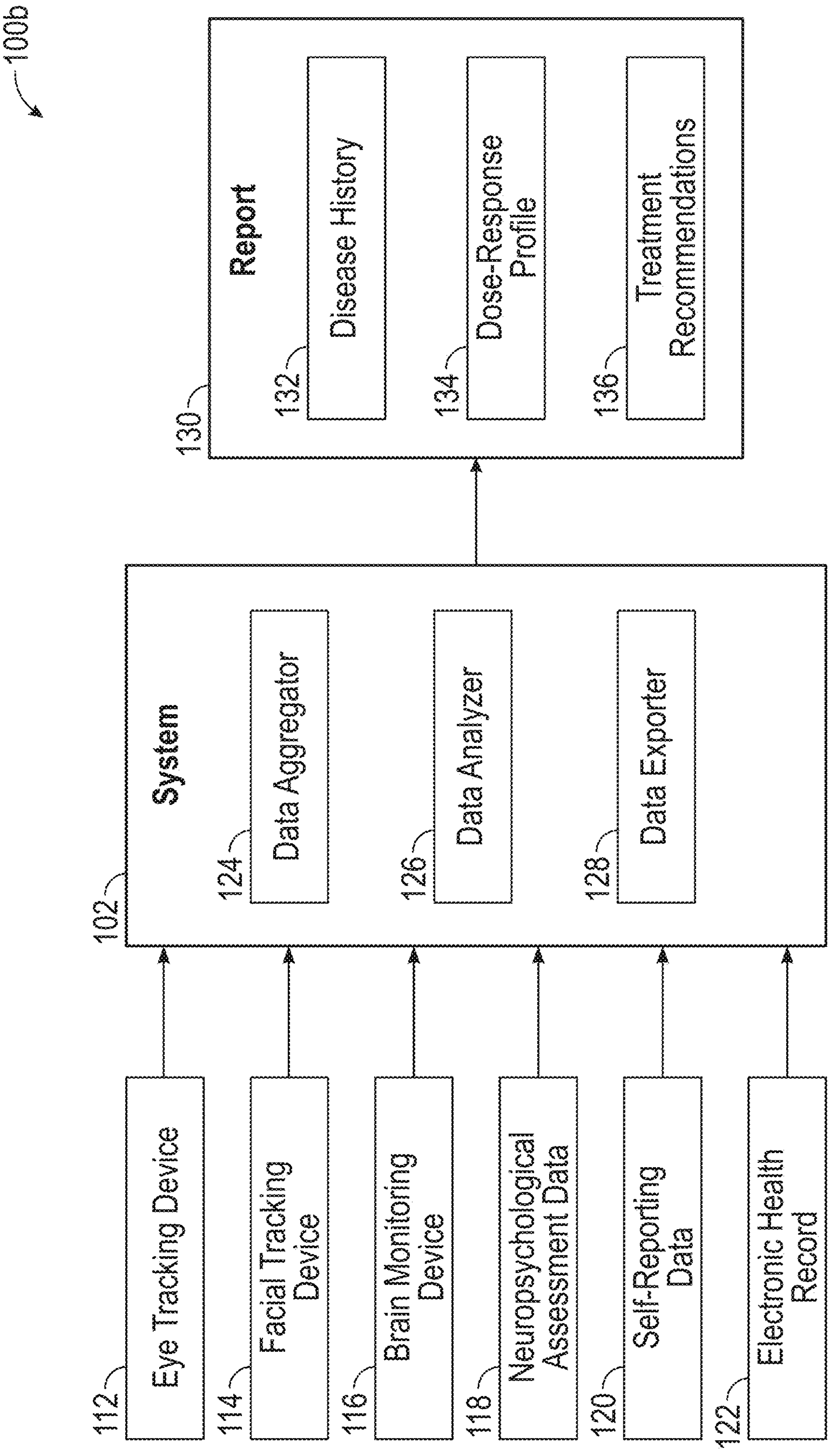
FIG. 1B is a schematic diagram of a data architecture that can be implemented by the system of FIG. 1A.
Figure 1C:
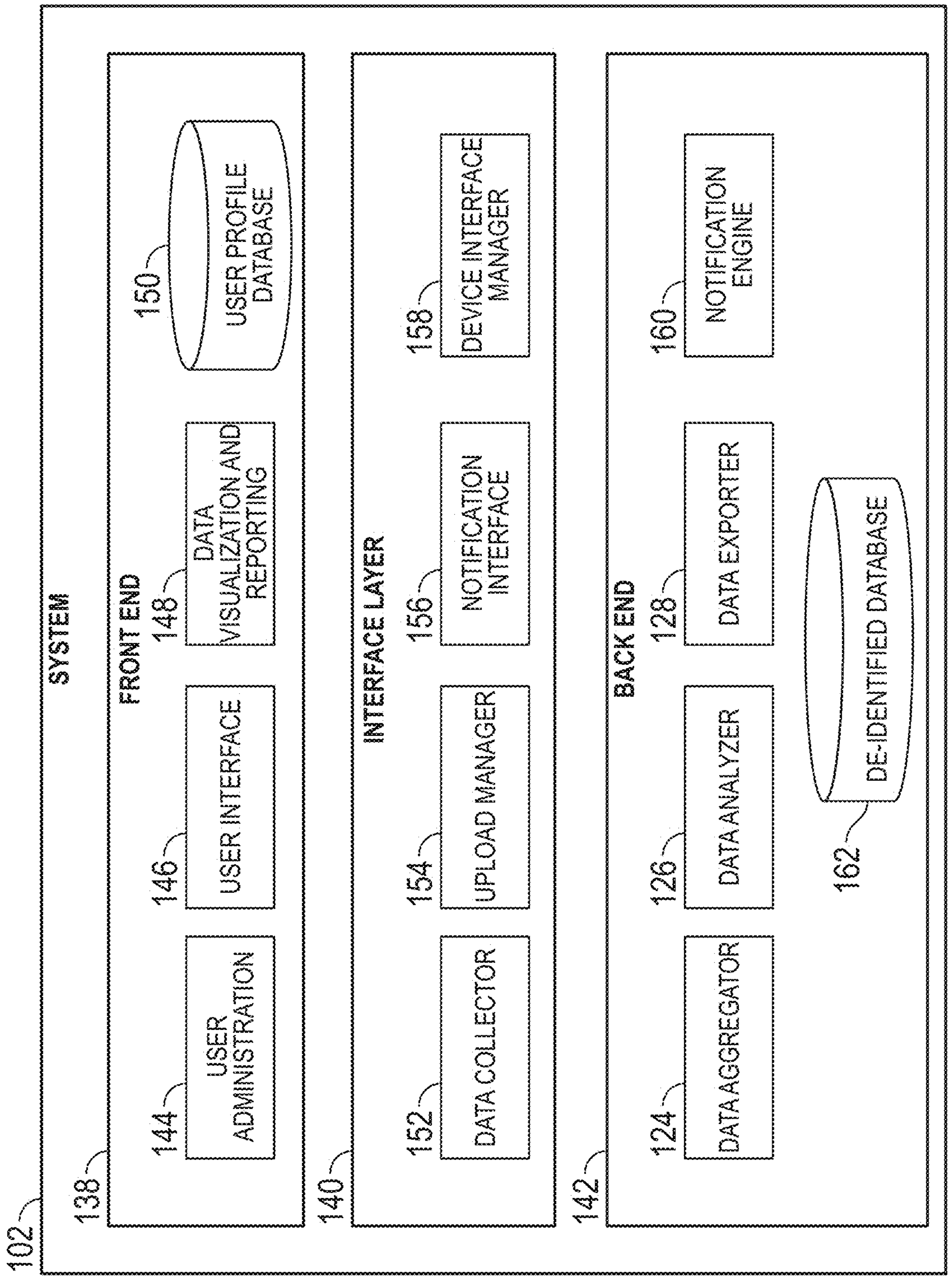
FIG. 1C is a schematic diagram of the components of the system of FIG. 1A.

II. Systems and Devices for Monitoring and Managing Neurological Diseases and Conditions FIGS. 1A-1C provide a general overview of a system for monitoring and managing neurological diseases and conditions ("system 102") configured in accordance with embodiments of the present technology. Specifically, FIG. 1A is a schematic diagram of a computing environment **100*a* in which the system 102 can operate, FIG. 1B is a schematic diagram of a data architecture 100*b* that can be implemented by the system 102, and FIG. 1C is a schematic diagram of the components of the system 102**.

Referring first to FIG. 1A, the system 102 is configured to monitor a patient who has been diagnosed with or is suspected of having a neurological disease or condition, such as epilepsy (e.g., absence epilepsy) or a disorder in which epilepsy is a symptom (e.g., Rett syndrome, tuberous sclerosis). Epilepsy may be classified into four types: focal epilepsy, generalized epilepsy, combined generalized and focal epilepsy, and unknown epilepsy. The system 102 can be or include one or more computing systems or devices having software and hardware components (e.g., processors, memory) configured to perform the various operations described herein. For example, the system 102 can be implemented as a distributed "cloud" server across any suitable combination of hardware and/or virtual computing resources. The system 102 can communicate with the other components within the computing environment **100*a* via a network 104. The network 104** can be or include one or more communications networks, such as any of the following: a wired network, a wireless network, a metropolitan area network (MAN), a local area network (LAN), a wide area network (WAN), a virtual local area network (VLAN), an internet, an extranet, an intranet, and/or any other suitable type of network or combinations thereof.

The system 102 is configured to receive and process various types of patient data. The patient data can include any data relevant to the patient's health and/or treatment. For example, the patient data can include any of the following: eye tracking data, facial tracking data, tracking data for other body parts (e.g., head, arms, hands, legs, feet, torso), physical activity data (e.g., whether the patient is moving, stationary, lying down), cardiovascular data (e.g., heart rate, blood pressure, blood oxygenation levels, electrocardiogram (ECG) data), breathing rate, body temperature (e.g., skin temperature), brain monitoring data (e.g., EEG data), EMG data, electrodermal data, biomarker levels in body fluids (e.g., sweat, blood, tears), neuropsychological assessment data, self-reporting data (e.g., seizure diaries), treatment plan data (e.g., medications, dosages, neurostimulation parameters), dietary data, electronic health records, demographic data, medical history, familial medical history, test results, imaging data (e.g., MRI data), genetic data, and/or any other suitable data type.

In some embodiments, the system 102 receives patient data from one or more patient monitoring devices (also referred to herein as "patient devices"). For example, in the illustrated embodiment, the system 102 is operably coupled to three patient devices **106*a*-106*c* (collectively, "patient devices 106"). In other embodiments, the system 102 can communicate with a different number of patient devices 106 (e.g., one, two, four, five, or more patient devices 106). The patient devices 106 can be or include any suitable device capable of monitoring the patient's health state. Examples of patient devices 106 suitable for use with the present technology include, but are not limited to: eye tracking devices (e.g., electrooculography (EOG)-based devices, video-based devices, laser-based devices, LIDAR-based devices), facial tracking devices, brain monitoring devices (e.g., EEG sensors), motion sensors (e.g., accelerometers, gyroscopes), activity sensors, cameras, heart rate sensors, blood pressure sensors, pulse oximeters, temperature sensors, ECG sensors, EMG sensors, electrodermal sensors, and electrochemical sensors. The patient devices 106 can have any suitable form factor, such as wearable devices (e.g., fitness trackers, smartwatches, smart glasses, smart contact lenses), implantable devices, non-implantable devices, fixed devices (e.g., devices that are attached to a wheelchair or other object), etc. The patient devices 106 can transmit the patient data to the system 102 continuously, at predetermined intervals (e.g., once per day, week, month), when new or updated data is available, when the system 102 sends a request to the patient device 106**, or any other suitable manner.

Optionally, the patient devices 106 can include one or more devices that do not directly sense the patient's health state, but instead receive health state data from another device or from a user. For example, the patient (or another user) can input data into a computing device (e.g., a mobile device, laptop, personal computing device), which in turn transmits the data to the system 102 via the network 104. As another example, a first patient device 106 (e.g., an eye tracking device) can transmit sensor data to a second patient device 106 (e.g., a mobile device) via wired or wireless communication techniques (e.g., Bluetooth, WiFi, USB) and the second patient device 106 can send the sensor data to the system 102 via the network 104. In such embodiments, the second patient device 106 can process the received sensor data before transmitting to the system 102, or can transmit the raw sensor data without processing.

In some embodiments, the system 102 also receives patient data from one or more healthcare provider devices. For example, in the illustrated embodiment, the system 102 is operably coupled to three healthcare provider devices **108*a*-108*c* (collectively, "healthcare provider devices 108"). In other embodiments, the system 102 can communicate with a different number of healthcare provider devices 108 (e.g., one, two, four, five, or more healthcare provider device 108). Each healthcare provider device 108 can be a computing system or device (e.g., a server, database) that is associated with a healthcare professional providing care for the patient, such as a primary care physician, neurologist, etc. For example, the healthcare professional can generate patient data such as electronic health records, neuropsychological assessments, test results, diagnoses, treatment plans, etc., that are stored at the healthcare provider devices 108. The healthcare provider devices 108 can transmit the patient data to the system 102 continuously, at predetermined intervals (e.g., once per day, week, month), when new or updated data is available, when the system 102 sends a request to the healthcare provider device 108**, or any other suitable manner.

The system 102 is configured to process and analyze the patient data received from the patient devices 106 and/or healthcare provider devices 108 to monitor the patient's health state over time. For example, based on the patient data, the system 102 can determine whether the patient has experienced, is experiencing, and/or is likely to experience a seizure event. As another example, the system 102 can monitor the patient during periods between seizure events (interictal periods) to assess the health state (e.g., neurocognitive state, encephalopathy) of the patient while the patient is exhibiting relatively normal function. Additional details of the data processing and analysis operations that can be performed by the system 102 are provided below.

Subsequently, the system 102 can generate a report for the patient including various types of information to assist a healthcare provider in managing the patient's disease or condition. For example, the report can include information regarding the history and progression of the patient's disease or condition over time. The report can also include a personalized, patient-specific dose-response profile that assesses how the patient responds to various treatments, in terms of therapeutic efficacy (e.g., seizure control) as well as toxicity (e.g., side effects). Optionally, the report can include recommendations for the patient's treatment that are predicted to improve efficacy and/or reduce toxicity.

The system 102 can store the patient data and/or analysis results (e.g., the report) in a database 110. As described in further detail below, the system 102 can implement one or more machine learning algorithms that are trained to process and/or analyze the stored data to perform various operations related to monitoring and/or managing a neurological disease or condition, such as identifying seizure events from patient data, measuring neurocognitive function from patient data, predicting patient responses to treatment, generating treatment recommendations, etc.

In some embodiments, the system 102 transmits the report to one or more of the healthcare provider devices 108 so the healthcare professional can evaluate the patient's condition, and, if appropriate, adjust the prescribed treatment regimen. The report can be transmitted at any suitable time interval, such as daily, weekly, bi-weekly, when updated data is available, in response to a request from the healthcare provider device 108, etc. Optionally, after reviewing the report, the healthcare professional can provide feedback to the system 102 via the healthcare provider device 108. For example, if the healthcare professional determines that the system 102 has incorrectly identified certain seizure events and/or side effects, the healthcare professional can send this feedback to the system 102 so the system 102 can update its analysis and generate a revised report. As another example, if the healthcare professional determines that a treatment recommended by the system 102 is not appropriate for the particular patient, the system 102 can update its treatment recommendation algorithm so the treatment is not recommended for that patient (and/or for similar patients) in the future.

Although FIG. 1A illustrates a single set of patient devices 106 that are used to collect data from a single patient, in other embodiments, the system 102 can be operably coupled to multiple sets of the patient devices 106, each set being associated with a different patient. Accordingly, the system 102 can be configured to receive and analyze patient data from a large number of patients, such as tens, hundreds, thousands, or tens of thousands of patients. In such embodiments, the database 110 can serve as a centralized repository for patient data from multiple patients. Optionally, the system 102 can analyze the patient data from multiple patients to generate population-level statistics, identify patterns and/or trends across large numbers of patients, use data from other patients to generate dose-response profiles, predictions, and/or treatment recommendations for a particular patient, etc. In some embodiments, data from multiple patients is used to create training data for the machine learning algorithms described herein.

Additionally, although FIG. 1A illustrates the system 102 as being directly connected to the database 110 without the network 104, in other embodiments the system 102 can be indirectly connected to the database 110 via the network 104. Additionally, any of the patient devices 106 and/or healthcare provider devices 108 can be configured to communicate directly with the system 102 and/or database 110, rather than communicating indirectly via the network 104.

FIG. 1B is a representative example of a data architecture 100*b* for the system 102, in accordance with embodiments of the present technology. In the illustrated embodiment, the system 102 receives patient data from a plurality of data sources, including an eye tracking device 112, a facial tracking device 114, a brain monitoring device 116, neuropsychological assessment data 118, self-reporting data 120, and/or an electronic health record 122.

The eye tracking device 112 can be any type of device configured to produce eye tracking data characterizing the movement, shape, and/or other relevant characteristics of one or both of the patient's eyes. For example, the eye tracking data can include any of the following types of data: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, relative eye movements, eye rolling, jerky eye movements, saccadic velocity, saccadic direction, torsional velocity, torsional direction, gaze direction, gaze scanning patterns, or eye activity during sleep. As discussed above, the eye tracking device 112 can use various types of sensor technologies, including, but not limited to, EOG, video, laser, and LIDAR. The form factor of the eye tracking device 112 can also be varied as desired, e.g., the eye tracking device 112 can be a wearable and/or mobile device (e.g., smart glasses, smart contact lens), or a fixed and/or stationary device (e.g., a device attached to a wheelchair, desktop, or other object separate from the patient's body).

The facial tracking device 114 can be any type of device configured to produce facial movement data characterizing the motion, shape, and/or other relevant features of the patient's face. For example, the facial movement data can include measurements of and/or changes in any of the following: distance between the patient's eyes, distance between the patient's eyelids, width of the patient's nose, center of the patient's nose, depth of the patient's eye sockets, shape of the patient's cheekbones, length of the patient's jawline, distance between the patient's mouth edges center of the patient's mouth, or focal weakness. The facial tracking device 114 can use various types of sensor technologies, such as video, movement sensors, EOG, and/or EMG. The facial tracking device 114 can be a wearable and/or mobile device, or a fixed and/or stationary device.

The brain monitoring device 116 can be any type of device configured to produce brain monitoring data characterizing the activity of the patient's brain. For example, the brain monitoring device 116 can be an EEG device that includes a plurality of electrodes configured to measure electrical activity of various parts of the brain. The brain monitoring device 116 can be a wearable and/or mobile device (e.g., an EEG headset or cap), a fixed and/or stationary device, or an implanted device.

The monitoring performed by the eye tracking device 112, facial tracking device 114, and/or brain monitoring device 116 can be performed during daytime, nighttime, while the patient is awake, while the patient is sleeping, while the patient is resting, while the patient is engaging in activities, and/or any other suitable time frame. The monitoring can be performed at any suitable frequency, such as once every 30 seconds, 1 minute, 2 minutes, 5 minutes, 10 minutes, 30 minutes, 1 hour, etc.

Although FIG. 1B illustrates the eye tracking device 112, facial tracking device 114, and brain monitoring device 116 as being three separate devices, in other embodiments, some or all of these devices can be integrated into a single device. For example, a single device can include sensors for eye tracking, facial tracking, and/or brain monitoring. Additionally, the system 102 can also receive data from other types of patient monitoring devices besides the eye tracking device 112, facial tracking device 114, and brain monitoring device 116.

The neuropsychological assessment data 118 can include results from performance-based neuropsychological tests, questionnaires, and/or other measures of the patient's neuropsychological function. The neuropsychological assessment data 118 can be collected using digital applications or manually (e.g., paper-based), and can be transmitted to the system 102 via a computing device associated with the healthcare professional that administered the assessment (e.g., a neuropsychologist).

The self-reporting data 120 can include any data produced by the patient that describes seizure events, side effects, tolerability, and/or information relevant to their health condition. For example, the self-reporting data 120 can include a seizure diary, responses to surveys/questionnaires, etc. In some embodiments, the patient or a caregiver inputs the self-reporting data 120 into a computing device (e.g., a mobile device, laptop, tablet), and the computing device transmits the self-reporting data 120 to the system 102 continuously or at predetermined time intervals.

The electronic health record 122 can include any clinical data stored in the patient's health record that is relevant to the patient's treatment. For example, the electronic health record 122 can include treatment plan data, such as the type(s) of medication prescribed to the patient, medication dosages, medication timing, type(s) of neurostimulation prescribed to the patient, neurostimulation parameters (e.g., location, timing, frequency, amplitude), and/or data regarding other treatment modalities (e.g., ketogenic diet). The electronic health record 122 can also include patient information, such as age, gender, weight, ethnicity, diagnoses, medical history, familial medical history, allergies, test results (e.g., genetic test results), and the like. In some embodiments, the electronic health record 122 is transmitted to the system 102 from a healthcare provider device.

The system 102 includes various software components for processing and/or analyzing the patient data received from the data sources. For example, as shown in FIG. 1B, the system 102 can include a data aggregator 124, a data analyzer 126, and/or a data exporter 128. The data aggregator 124 processes incoming data to ensure it is stored appropriately (e.g., data for a single patient that is received at different times and/or from different data sources can be stored at the same location and/or labeled to indicate that the data belongs to the same patient). Optionally, the data aggregator 124 can perform additional functions, such as filtering the incoming data to remove data that is erroneous, incomplete, or otherwise unsuitable for downstream processing.

The data analyzer 126 analyzes the patient data using statistical analysis, pattern recognition, machine learning, and/or other techniques to perform various operations, such as detecting recognizable patterns consistent with seizure events and generating seizure data indicative of the patient's seizure burden, including timestamps of seizure events, number of seizure events, duration of seizures, etc. The data analyzer 126 can also analyze the patient data to assess the patient's neurological functioning using measures such as reading speed, processing speed, attention, executive function, gaze path during scene scanning, and/or drowsiness. Based on this information, the data analyzer 126 can determine the patient's baseline state (e.g., seizure burden and/or cognition assessment prior to treatment), identify changes in the patient's state in response to specific treatment, and/or provide recommendations for the patient's treatment to improve seizure control and/or reduce side effects. Additional details of analytical methods that may be implemented by the data analyzer 126 are described in Section III below.

The data exporter 128 generates an electronic report 130 summarizing the results of the analysis performed by the data analyzer 126. For example, the report 130 can include a disease history 132 describing the progression of the patient's disease or condition over time (e.g., changes in seizure burden, side effects such as neurocognitive impacts, medications taken). The report 130 can also include a personalized dose-response profile 134 describing how the patient's state (e.g., seizure burden, neurocognitive function) varies with respect to medication dosage and/or other treatment modalities. Optionally, the report 130 can include a set of treatment recommendations 136 for improving seizure control and/or reducing side effects experienced by the patient. The data exporter 128 can output the report 130 in any suitable format, including textual summaries, statistics, structured data (e.g., tables, charts, database), visualizations (e.g., graphs), and the like. The content and/or format of the report 130 can be customized based on the intended recipient (e.g., patient, healthcare provider, pharmacist, etc.). The report 130 can be transmitted to an external system or device (e.g., a healthcare provider device or other user computing device) for use in monitoring and managing the patient's disease or condition.

FIG. 1C is a block diagram that schematically illustrates the components of the system 102, in accordance with embodiments of the present technology. The system 102 can include a front end 138, an interface layer 140, and a back end 142. The front end 138 can include a user administration component 144, a user interface 146, a data visualization and reporting component 148, and/or a user profile database 150. The user administration component 144 can manage how users (e.g., patients, caregivers, healthcare providers) access the system 102. The user interface 146 can allow users to interact with the system 102 via the user's computing system or device (e.g., a healthcare provider device, patient device). The data visualization and reporting component 148 can present data (e.g., reports, graphs, statistics) for review by the user. The user profile database 150 can include user information such as name, login information, user type (e.g., patient, healthcare provider), access rights, and the like.

The interface layer 140 can include a data collector 152, upload manager 154, notification interface 156, and/or device interface manager 158. The data collector 152 can manage collection of patient data from various sources (e.g., patient devices, healthcare provider devices, etc.). The upload manager 154 can manage uploading of data to the system 102 from various sources. The notification interface 156 can output alerts, messages, and/or other user notifications. The device interface manager 158 can control communications with external systems and/or devices, such as patient devices (e.g., eye tracking devices, facial tracking devices), healthcare provider devices, etc.

The back end 142 can include the data aggregator 124, data analyzer 126, and/or data exporter 128 previously described with respect to FIG. 1B. Additionally, the back end 142 can include a notification engine 160, and/or a de-identified database 162. The notification engine 160 can generate user notifications for output via the notification interface 156. The de-identified database 162 can provide a repository for storing patient data including personal medical information according to patient privacy requirements.

Figure 2:
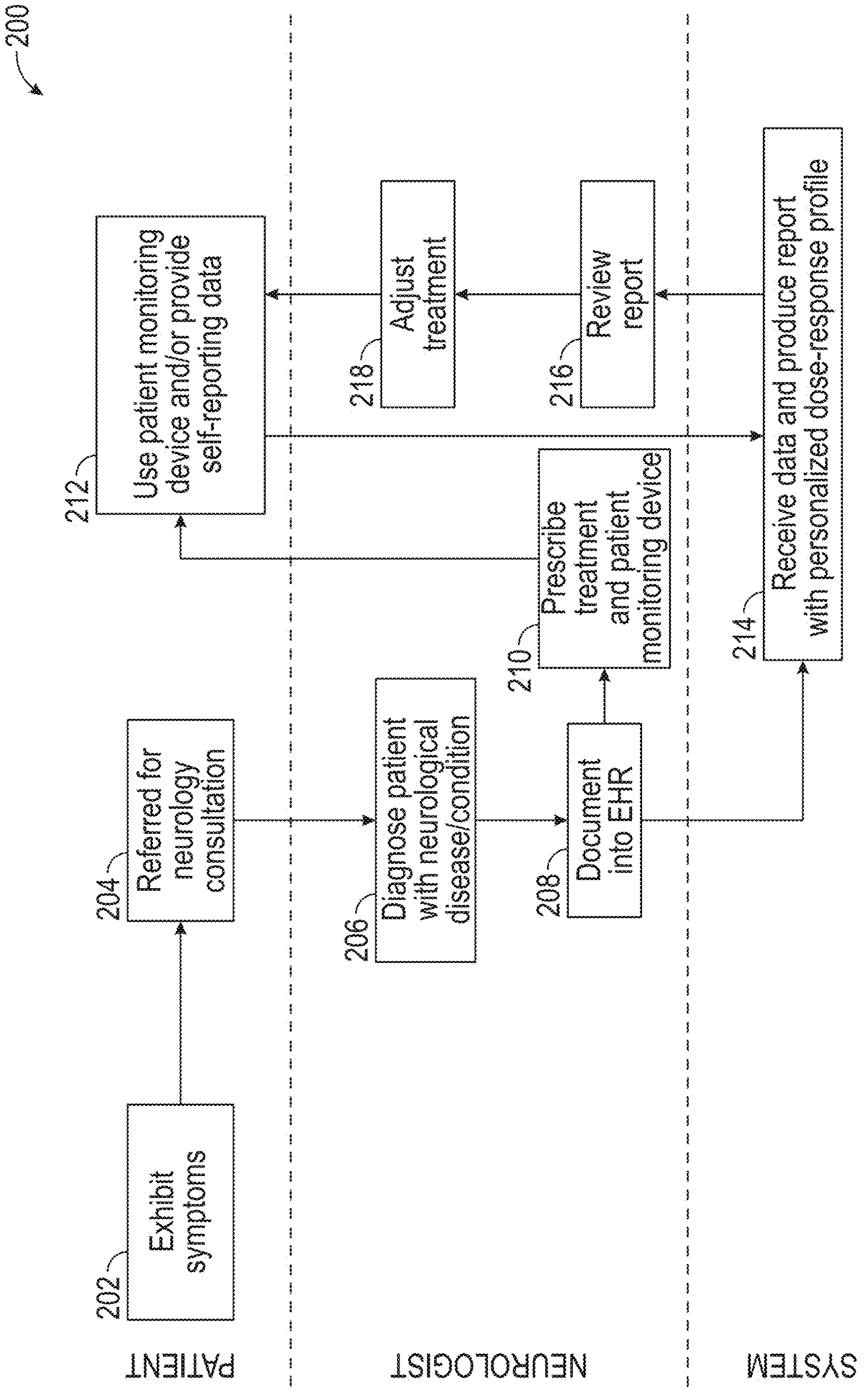
FIG. 2 is a flow diagram illustrating an example clinical workflow for monitoring and managing a patient's neurological disease or condition, in accordance with embodiments of the present technology

III. Methods for Monitoring and Managing Neurological Diseases and Conditions FIG. 2 is a flow diagram illustrating an example clinical workflow 200 for monitoring and managing a patient's neurological disease or condition using the system 102 of FIGS. 1A-1C, in accordance with embodiments of the present technology. The workflow 200 begins at block 202 with the patient exhibiting symptoms indicative of seizure activity, such as staring spells, daydreaming, poor performance, convulsions, and/or previous seizure history. At block 204, after seeking care (e.g., at an emergency room or with a primary care physician), the patient is referred for a neurology consultation and/or related testing (e.g., routine EEG).

At block 206, at the initial visit with the neurologist (or other appropriate healthcare professional), the neurologist diagnoses the patient with a neurological diseases or condition based on the patient's clinical history, a physical examination, test results (e.g., EEG report, imaging reports, genetic testing results), and/or other relevant information. At block 208, the neurologist can document the patient's diagnosis and other relevant patient information into the patient's electronic health record (EHR).

At block 210, the neurologist can prescribe a treatment (e.g., an initial medication and dosage titration schedule) for the patient. The neurologist can also instruct the patient to use a patient monitoring device (e.g., eye tracking device, facial tracking device, etc.), including the frequency and duration the device is to be used. Measurements of the patient's baseline condition (e.g., measurements generated before the patient initiates treatment) can be obtained while the patient is at the clinic or at the patient's home.

At block 212, the patient uses the patient monitoring device as prescribed by the neurologist. For example, the patient can wear an eye tracking device for two hours a day for two days per week. As previously discussed, the device can generate patient data (e.g., eye movement data, facial movement data, etc.) that is transmitted to the system 102 for processing and analysis. Optionally, the patient (or a caregiver for the patient) can provide self-reporting data such as seizure counts, side effects, tolerability, etc. The data can be provided to the system 102 via manual entry into a software application connected to the system 102.

At block 214, the system 102 receives patient data from various sources, including the patient monitoring device, self-reporting data, and EHR data. The system 102 can assess the patient's baseline condition and monitor the patient's response to the treatment over time in order to generate a report with a personalized dose-response profile for the patient. In some embodiments, the report describes the patient's response (e.g., seizure burden and/or side effects) to a particular therapy and dosage. Patients can also be identified as unresponsive to treatment, or experiencing a decline in cognition and/or seizure control despite increasing dosage, which may suggest progression of natural history of the disease or condition.

At block 216, the neurologist can receive and review the report over defined intervals (e.g., daily, weekly, bi-weekly, monthly) to monitor the patient's seizure burden, cognition, and/or side effects over time. If appropriate, at block 218, the neurologist can adjust the patient's treatment based on the information in the report. For example, the neurologist can use the personalized dose-response profile to determine the optimal therapeutic dose for the patient (e.g., a dose that provides improved seizure control or seizure freedom) while reducing or minimizing side effects. The processes of blocks 212-218 can be repeated over time to continuously monitor the patient's condition and adjust the treatment.

Figure 3:
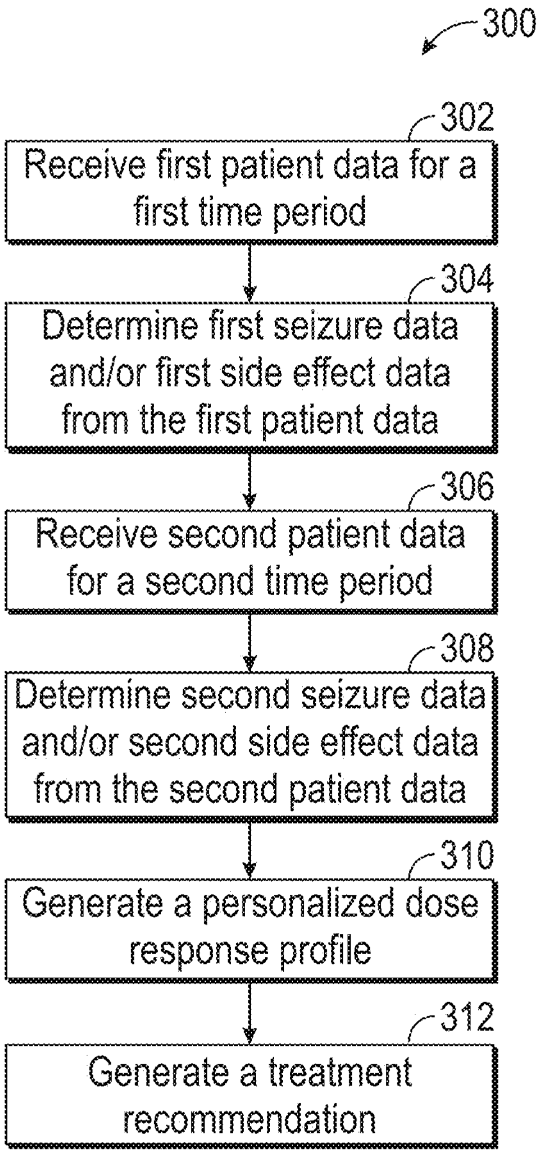
FIG. 3 is a flow diagram illustrating a method for monitoring a patient having a neurological disease or condition, in accordance with embodiments of the present technology.

FIG. 3 is a flow diagram illustrating a method 300 for monitoring a patient having a neurological disease or condition, in accordance with embodiments of the present technology. The method 300 can be performed by any embodiment of the systems and devices described herein, such as by a computing system or device including one or more processors and a memory storing instructions that, when executed by the one or more processors, cause the computing system or the device to perform some or all of the steps described herein. For example, some or all of the steps of the method 300 can be performed by the system 102 of FIGS. 1A-1C.

The method 300 begins at block 302 with receiving first patient data for a first time period. The first patient data can include any of the patient data types described herein (e.g., eye movement data, facial movement data, brain monitoring data, self-reporting device, etc.). In some embodiments, the first patient data is received from one or more patient monitoring devices that are worn by or otherwise associated with the patient, such as an eye tracking device, facial tracking device, brain monitoring device, and/or any of the other devices previously described herein. Alternatively or in combination, the first patient data can be received from other data sources, such as a healthcare provider device.

In some embodiments, the first patient data is used to determine the patient's baseline health state, such as the patient's baseline seizure burden and/or baseline neurocognitive function. The baseline health state can be used as a point of comparison for assessing the therapeutic and/or toxic effects of a treatment of interest, as described further below. Accordingly, the first patient data can be generated during a baseline time period, such as a time period before the patient has started a treatment of interest (e.g., medication, neurostimulation) for the neurological disease or condition. Optionally, the patient may already be undergoing treatment during the baseline time period (e.g., taking an initial dosage of a medication), such that the patient's response to subsequent treatment is assessed relative to the patient's state with the initial treatment, rather than relative to the patient's state without any treatment.

The first time period can be any time period that is long enough to collect sufficient data to accurately characterize the patient's baseline health state. For example, the first time period can be at least 1 day, 2 days, 3 days, 4 days, 5 days, 6 days, 1 week, 2 weeks, 3 weeks, 4 weeks, or 1 month. The first patient data can be generated at any suitable frequency over the first time period, such as once every 15 minutes, once every 30 minutes, once every hour, once every 2 hours, once every 12 hours, or once every day. In some embodiments, the first patient data is generated over a prescribed duration for each day, e.g., 1 hour, 2 hours, 6 hours, or 12 hours for each day of the first time period. Different types of patient data can be collected at different frequencies and/or for different durations, e.g., eye tracking data may be collected more frequently than brain monitoring data, etc.

At block 304, the method 300 continues with determining first seizure data and/or first side effect data from the first patient data. The first seizure data can include data characterizing one or more seizure events experienced by the patient during the first time period, such as data regarding the type, number, frequency, duration (e.g., preictal duration, ictal duration, and/or postictal duration), timing, severity, and/or variability of seizure events. Examples of seizure events that may be determined using the techniques described herein include, but are not limited to, absence seizures, atypical absence seizures, tonic-clonic seizures, clonic seizures, tonic seizures, atonic seizures, myoclonic seizures, simple partial seizures, complex partial seizures, secondary generalized seizures, and infantile spasms. In some embodiments, the first seizure data includes a measurement of the patient's seizure burden during the first time period, such as the frequency of seizures per unit time, the total duration of seizures per unit time, severity of loss of consciousness associated with seizures, severity of postictal state, and/or any other quantitative measure of seizure burden known those of skill in the art. Seizure counts plotted over a longer time period (e.g., days or weeks) can in turn be used to measure data such as baseline seizure burden, duration of seizure, and/or postictal duration and severity (e.g., following seizure abnormalities).

The first seizure data can be determined from the first patient data using any suitable technique. For example, the first patient data can include eye movement data, and the first seizure data can be automatically determined from the eye movement data using pattern recognition, statistical analysis, machine learning algorithms, or combinations thereof. In some embodiments, the eye movement data produced by an eye tracking device is converted into a time series of patient eye movements, also referred to herein as "oculometric data." Subsequently, a seizure detection algorithm can be used to mathematically analyze the oculometric data to identify eye movement patterns that are characteristic of seizure events. For example, a loss of normal eye activity (e.g., decrease in noisiness of eye movements) can correlate to the occurrence of an absence seizure. Eye movement patterns associated with seizure events can be detected by changes in kurtosis, correlation, and/or other statistics calculated from eye movement data. The output of the seizure detection algorithm can be timing data (e.g., timestamps) indicating the occurrence and duration of the seizure event.

In some embodiments, the seizure detection algorithm can include at least one machine learning algorithm that has been trained on previous patient data (e.g., seizure data from the same patient and/or from other patients) to identify seizure events from eye movement data. The machine learning algorithm can be trained via supervised learning, unsupervised learning, semi-supervised learning, reinforcement learning, and/or transfer learning. Examples of machine learning algorithms suitable for use with the present technology include, but are not limited to, time-series algorithms (e.g., long short-term memory (LSTM), gated recurrent units (GRU)), convolutional neural networks (CNNs) (e.g., ResNet-50, GoogLeNet), and clustering algorithms (e.g., k-means clustering).

For example, the machine learning algorithm can be trained to identify seizure events from the eye movement data obtained over a particular time segment. The size of the time segment can be predetermined based on the expected duration of the seizure event, or can be determined dynamically based on the actual patient data. The input to the machine learning algorithm can include the eye movement time-series data, as well as features and/or statistics calculated from the time-series data (e.g., pupil size, pupil location, eccentricity, blink frequency). Optionally, the time-series data can be transformed (e.g., such as using a Fast Fourier Transform, a wavelet transform such as continuous wavelet transform (CWT)), and the transformed data (e.g., frequency domain data, scalogram data) can be used as the input to the machine learning algorithm. Optionally, the input data can also include other data types, such as video data of the eyes and/or face. Based on the input data, the machine learning algorithm can determine whether a seizure event occurred during the time segment, and, optionally, an associated confidence value.

Additional examples of methods for determining seizure events from eye movement data are described in U.S. Patent Application Publication No. 2021/0000341, U.S. patent application Ser. No. 17/381,562, U.S. Provisional Application No. 63/239,158, and U.S. Provisional Application No. 63/243,896, the disclosures of each of which are incorporated by reference herein in their entirety.

Figure 4A:
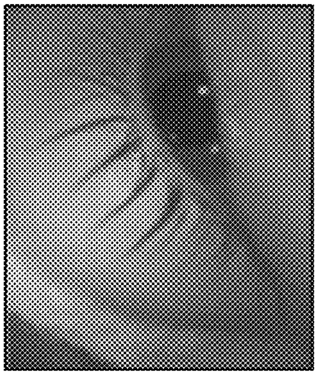
FIGS. 4A-4G illustrate an example of seizure detection from eye movement data, in accordance with embodiments of the present technology
Figure 4B:
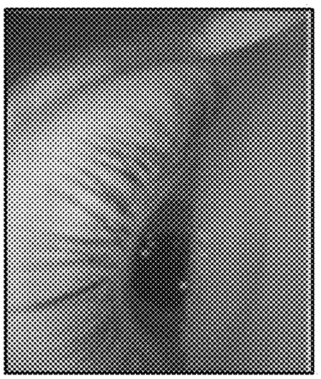

FIGS. 4A-4G illustrate an example of seizure detection from eye movement data, in accordance with embodiments of the present technology. Referring first to FIGS. 4A and 4B, the eye movement data was produced by a video-based eye-tracking device that monitored movement of the patient's right eye (FIG. 4A) and left eye (FIG. 4B) over time. The device monitored more than 20 oculometric data points, including pupil area to iris area ratio, pupil constriction/dilation rate and velocity, pupil diameter, saccadic and torsional velocity and direction, eye blink rate, and duration. The eye movement data was processed using a seizure detection algorithm that identified the pause/stare of absence seizure events by measuring a reduced frequency of saccades derived from the relative x/y position of the eye.

Figure 4C:
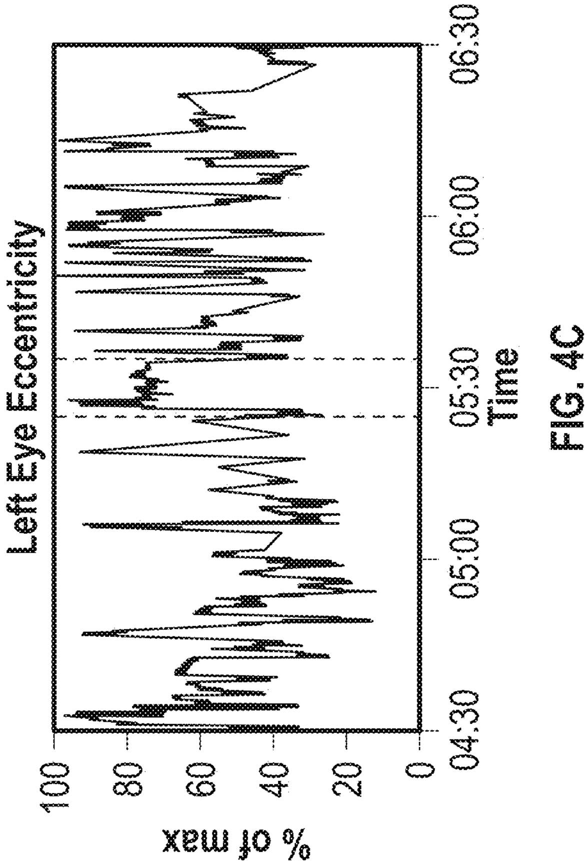
Figure 4D:
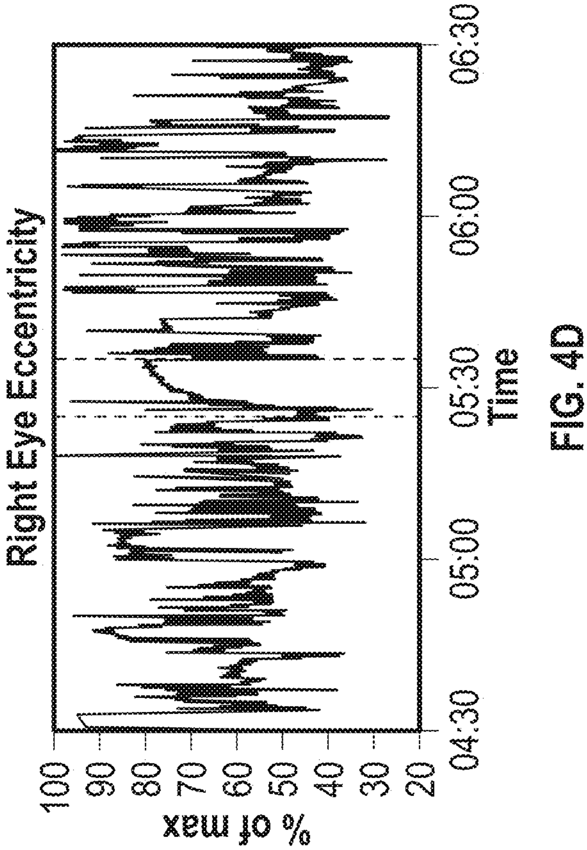

FIGS. 4C and 4D are graphs of oculometric data for the left eye (FIG. 4C) and right eye (FIG. 4D). The vertical axis is eye eccentricity as a percentage of maximum eccentricity, and the horizontal axis is time in 30 second increments. The vertical broken lines indicated the occurrence of a seizure event around 5:30, as confirmed by EEG. Eccentricity is a calculated function of the horizontal and vertical width of the pupil, and can depend on (1) occlusion of the pupil relative to the eyelid, (2) pupil area, and (3) blink frequency. Thus, eccentricity can be a combination of multiple oculometric features (e.g., pupil size, pupil location, eyelid location). As shown in FIGS. 4C and 4D, the onset of the seizure event correlated to a decrease in the variability of eye eccentricity, and the conclusion of the seizure event correlated to the return of variability in the eye eccentricity.

Figure 4F:
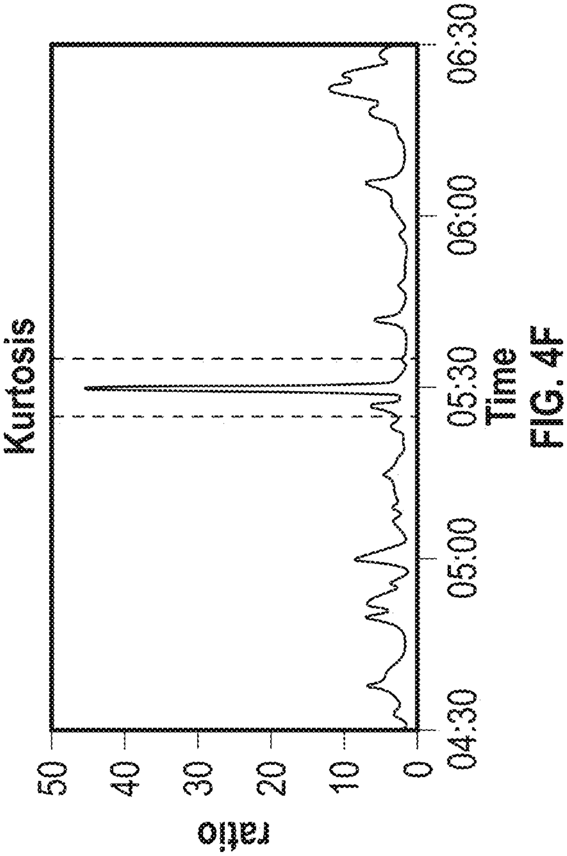
Figure 4E:
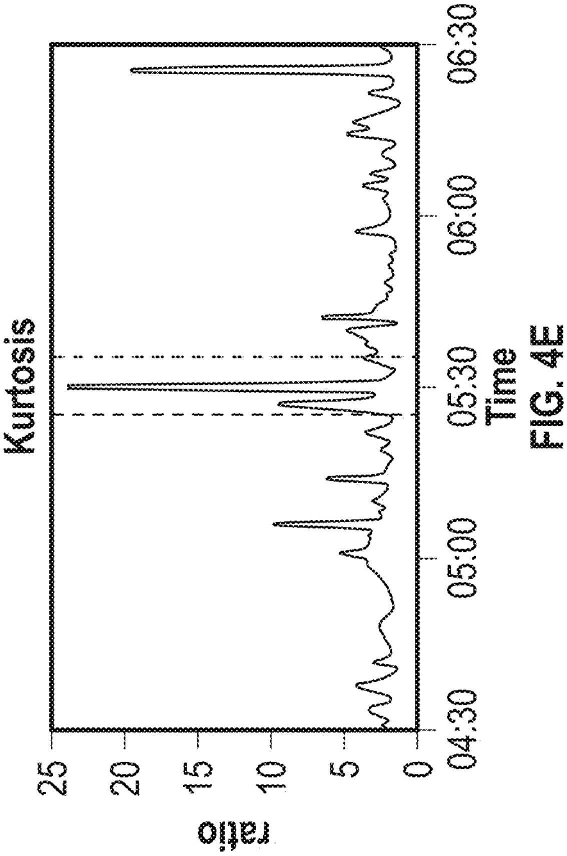

FIGS. 4E and 4F are graphs of the kurtosis of the eccentricity for the left eye (FIG. 4E) and right eye (FIG. 4F). Kurtosis is a statistical measure that can be used to analyze stability of an oculometric parameter over a measured window, with an inverse relationship to variability (e.g., small kurtosis correlates to high variability, large kurtosis correlates to low variability). As shown in FIGS. 4E and 4F, the onset of the seizure event produced a more than 4-fold increase in the kurtosis of eccentricity compared to non-seizure timeframe.

Figure 4G:
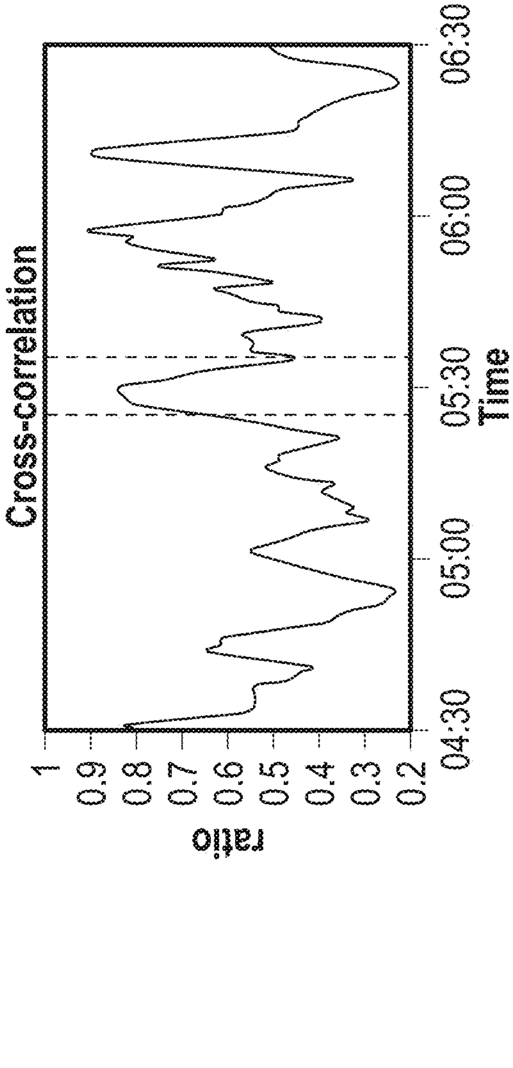

FIG. 4G is a graph of cross-correlation of eccentricity between the left and right eyes. In some embodiments, an increase in concordance of left and right eye movements can indicate the onset of a seizure event.

Referring again to block 304 of FIG. 3, in some embodiments, the first seizure data can be determined using other types of patient data, in addition or as an alternative to eye movement data. For example, the techniques described herein (e.g., statistical analysis, pattern recognition, machine learning) for identifying seizure events can also be applied to facial movement data, brain activity data, motion data, EMG data, electrodermal data, and/or any of the other patient data types previously discussed herein. Seizure events can also be identified based on patient self-reporting data. For example, the self-reporting data can be used to identify candidate time segments that are then analyzed in detail using eye tracking data and/or other patient monitoring data to confirm whether a seizure event did indeed occur, and, if so, the characteristics of that event.

As described in greater detail below, the patient's seizure burden can be assessed over time as therapeutics are initiated to measure treatment efficacy and/or toxicity. For example, efficacious treatments would be expected to reduce the patient's seizure burden, as indicated by decreases in seizure counts, seizure duration, and/or postictal duration. Conversely, certain treatments (e.g., anticonvulsant medications) may exhibit toxicity that increases the patient's seizure burden, as indicated by worsening of seizure counts, seizure duration, and/or postictal duration.

In some embodiments, block 304 also includes determining first side effect data from the first patient data. The first side effect data can include data characterizing one or more side effects experienced by the patient during the first time period, such as data regarding the type, timing, duration, frequency, and/or severity of a side effect experienced by the patient. Side effects can include any undesirable effect of a treatment regimen (e.g., medication) on a patient's function, including impacts on neurocognitive function, motor function, and/or mood. In embodiments where the first patient data is obtained during a baseline time period before the patient has started a treatment of interest, the first side effect data can include data characterizing the patient's current level of function (e.g., neurocognitive function, motor function, etc.) that may be impacted once the patient starts the treatment. Examples of side effects that may be determined using the techniques described herein include, but are not limited to, drowsiness, a decrease in cognition, a decrease in attention, a decrease in concentration, a change in mood, a change in behavior, loss of consciousness, suicidality, homicidality, irritability, or a change in vision.

The first side effect data can be determined from the first patient data using any suitable technique. For example, the first patient data can include eye movement data, and the first side effect data can be automatically determined from the eye movement data using pattern recognition, statistical analysis, machine learning algorithms, or combinations thereof. In some embodiments, an interictal analysis algorithm can be used to mathematically analyze eye movement data to (1) detect time periods during which the patient is not experiencing a seizure event (interictal time periods) and (2) identify eye movement patterns during those time periods that correlate to patient states and/or activities that can be used to characterize the patient's function. For example, eye movement patterns can be used to characterize the patient's level of drowsiness, ability to scan natural environments, and reading ability, which in turn may be indicative of the patient's neurocognitive state, as described in further detail below. The output of the interictal analysis algorithm can be data indicating (1) the type of patient state/activity observed from the eye movement data, and (2) a quantitative and/or qualitative assessment of the patient's function based on the observed state/activity.

In some embodiments, the interictal analysis algorithm can include at least one machine learning algorithm that has been trained on previous patient data (e.g., interictal data from the same patient and/or from other patients) to evaluate the side effects experienced by a patient and/or the patient's current level of function based on eye movement data. The machine learning algorithm can be trained via supervised learning, unsupervised learning, semi-supervised learning, reinforcement learning, and/or transfer learning. Examples of machine learning algorithms suitable for use with the present technology include, but are not limited to, time-series algorithms (e.g., LSTM, GRU), convolutional neural networks (e.g., ResNet-50, GoogLeNet), and clustering algorithms (e.g., k-means clustering).

For example, a machine learning algorithm can be trained to identify specific patient states and/or activities from the eye movement data obtained over a particular time segment (e.g., whether the patient is currently reading, awake, sleeping, feeling drowsy, etc.). The size of the time segment can be predetermined based on the expected duration of the patient state/activity of interest, or can be determined dynamically based on the actual patient data. The machine learning algorithm can also be trained to assess the patient's functional level, based on the eye movement data during the time segment while the patient is in a particular state and/or performing a particular activity, and/or based on the duration of time spent in particular states and/or activities. The input to the machine learning algorithm can include the eye movement time-series data, features and/or statistics calculated from the time-series data, and/or transformations of the time-series data, as previously discussed. Optionally, the input data can also include other data types, such as video data of the eyes and/or face. Based on the input data, the machine learning algorithm can determine the types and/or severities of functional impairments and/or other side effects experienced by the patient. Optionally, this analysis can be performed by an ensemble of machine learning algorithms, rather than a single machine learning algorithm. For example, a first machine learning algorithm can be trained to classify patient states/activities from eye movement data, and one or more second machine learning algorithms can be trained to assess the patient's functional level based on eye movement data of a particular patient state/activity (e.g., one machine learning algorithm is used to assess drowsiness, another machine learning algorithm is used to assess reading ability, and so on).

Figure 5A:
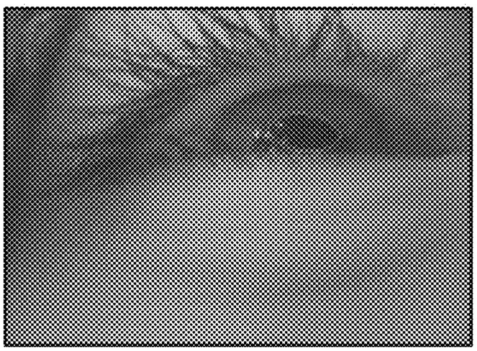
FIGS. 5A-5D illustrate an example of drowsiness detection from eye movement data, in accordance with embodiments of the present technology.
Figure 5B:
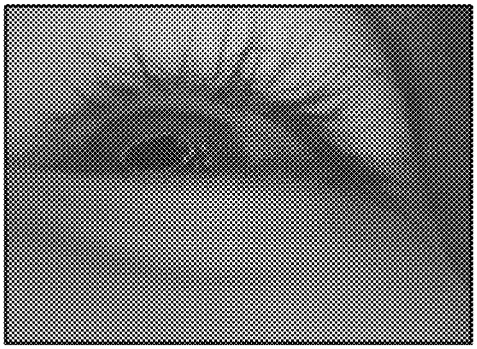
Figure 5C:
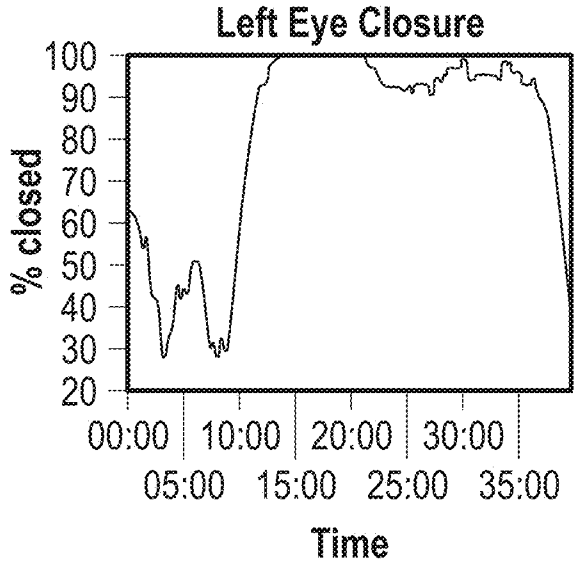
Figure 5D:
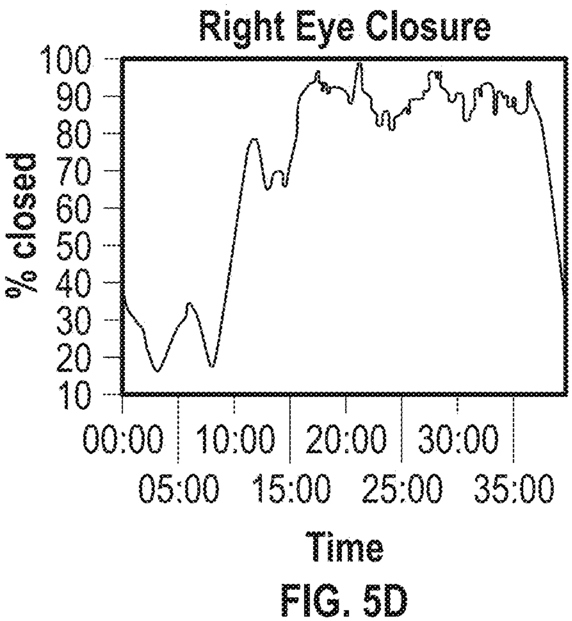

FIGS. 5A-5D illustrate an example of drowsiness detection from eye movement data, in accordance with embodiments of the present technology. Referring first to FIGS. 5A and 5B, the eye movement data was produced by a video-based eye-tracking device that monitored movement of the patient's right eye (FIG. 5A) and left eye (FIG. 5B) over time. FIGS. 5C and 5D are graphs of oculometric data for the left eye (FIG. 5C) and right eye (FIG. 5D). The vertical axis is percent eye closure time, and the horizontal axis is time. Values above 80% are consistent with eye closure. In some embodiments, values near or above 80% are indicative of drowsiness and/or fatigue. Drowsiness can be used to characterize side effects such as lethargy, fatigue, disturbed sleep, sleep apnea, and/or other sleep-related behaviors. Total drowsiness can be recorded over a number of days, and, as discussed further below, compared to timing and/or dosing of treatments as an indication of toxicity and/or resulting impairment in normal daily functioning.

Figure 6:
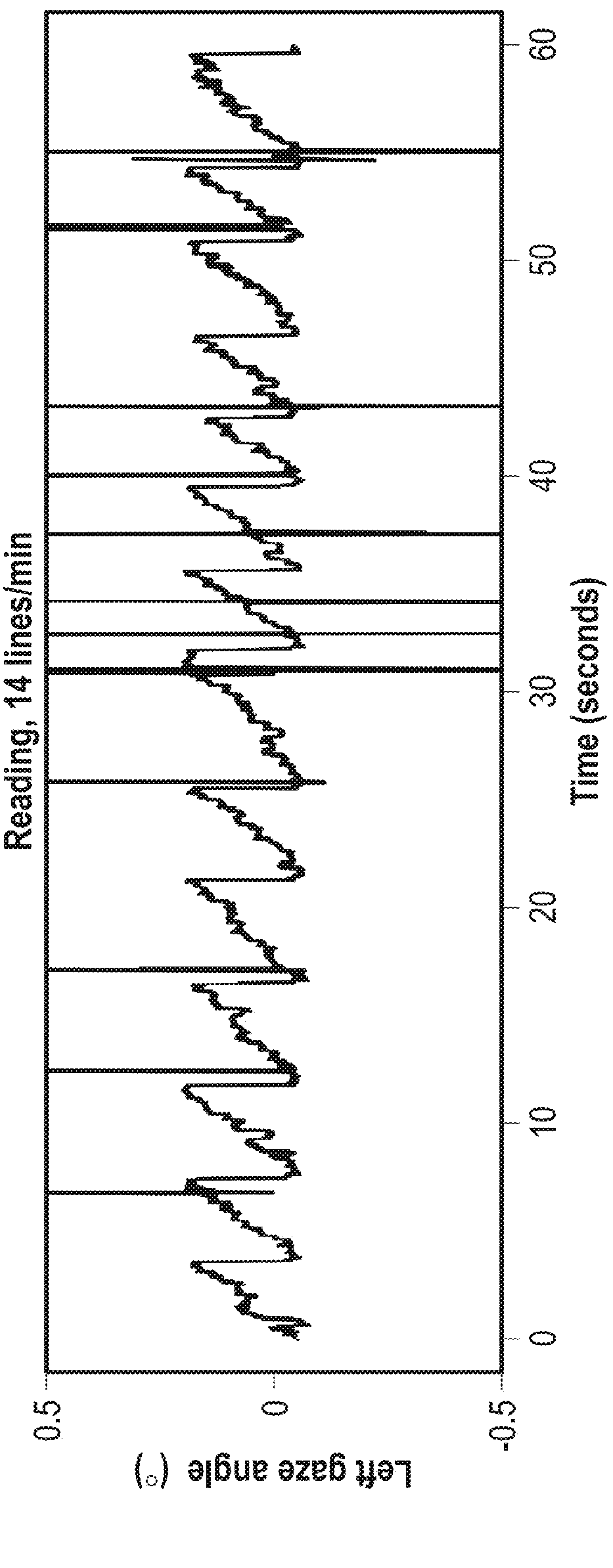
FIG. 6 illustrates an example of reading ability detected from eye movement data, in accordance with embodiments of the present technology.

FIG. 6 illustrates an example of reading ability detected from eye movement data, in accordance with embodiments of the present technology. As shown in FIG. 6, reading can be associated with a particular eye movement pattern, such that reading speed, duration, and/or accuracy can be measured over time using oculometric parameters such as eye gaze angle, fixation duration, saccade size, saccade accuracy, and/or direction of saccades. In some embodiments, aspects of reading ability such as reading speed and/or duration can be used as a surrogate for neurocognitive parameters, including, but not limited to, reading skill, processing speed, memory, and/or attention. As discussed further below, reading ability can be measured at baseline and then over time to show therapeutic toxicity and/or efficacy as it relates to cognition. In some embodiments, reduced reading ability (e.g., decreased reading speed and/or attention) correlates to side effects and/or disease progression, while improved reading ability (e.g., increased reading speed and/or attention) correlates to improved seizure control and/or a reduction in side effects (e.g., due to reduction in medications, conversion to monotherapy from polytherapy, etc.).

Referring again to block 304 of FIG. 3, in some embodiments, the first side effect data can be determined using other types of patient data, in addition or as an alternative to eye movement data. For example, the techniques described herein (e.g., statistical analysis, pattern recognition, machine learning) for identifying seizure events can also be applied to facial movement data, brain activity data, motion data, EMG data, electrodermal data, and/or any of the other patient data types previously discussed herein. Side effects can also be determined based on other aspects of the patient's voluntary and/or involuntary behaviors (e.g., movements, sleep patterns, cell phone habits). Side effects can also be evaluated based on neuropsychological assessment data, surveys, questionnaires, and/or other tests that directly assess the patient's current functional state. Optionally, patient self-reporting data can be used to identify side effects experienced by the patient and/or determine the severity and/or tolerability of side effects. For example, patient self-reporting data can provide feedback to correlate the observed side effects with the patient's personal tolerability thresholds, e.g., a side effect that appears mild based on patient monitoring data may be perceived as being highly intolerable, or vice-versa.

At block 306, the method 300 includes receiving second patient data for a second time period. The process of block 306 can be identical or generally similar to the process of block 302. For example, the second patient data can include any of the patient data types described herein (e.g., eye movement data, facial movement data, brain monitoring data, self-reporting device, etc.), and can be received from any suitable device (e.g., patient monitoring devices, healthcare provider devices, etc.). In some embodiments, the second patient data includes the same patient data types and/or is received from the same devices as first patient data. In other embodiments, the second patient data can include different patient data types and/or can be received from different devices than the first patient data.

In some embodiments, the second patient data is used to determine the patient's health state (e.g., seizure burden, neurocognitive function) after a treatment of interest has been initiated, also referred to herein as the patient's "treatment health state." The treatment health state can be compared against the baseline health state for assessing the therapeutic and/or toxic effects of the treatment regimen, as described further below. Accordingly, the second patient data can be generated during a treatment time period, such as a time period after the patient has started a treatment of interest (e.g., medication, neurostimulation) for the neurological disease or condition. The treatment time period can be selected so that the patient is expected to have reached steady state with respect to the treatment (e.g., two to five days after starting a dosage of a medication). Optionally, in embodiments where the patient was already undergoing treatment during the baseline time period (e.g., taking an initial dosage of a medication), the treatment time period can occur after an adjustment to the patient's treatment (e.g., taking a different dosage of a medication, switching to a different medication, stopping a medication, etc.).

The second time period can be any time period that is long enough to collect sufficient data to accurately characterize the patient's treatment health state. For example, the second time period can be at least 1 day, 2 days, 3 days, 4 days, 5 days, 6 days, 1 week, 2 weeks, 3 weeks, 4 weeks, or 1 month. The second patient data can be generated at any suitable frequency over the second time period, such as once every 15 minutes, once every 30 minutes, once every hour, once every 2 hours, once every 12 hours, or once every day. In some embodiments, the second patient data is generated over a prescribed duration for each day, e.g., 1 hour, 2 hours, 6 hours, or 12 hours for each day of the first time period. Different types of patient data can be collected at different frequencies and/or for different durations, e.g., eye tracking data may be collected more frequently than brain monitoring data, etc.

At block 308, the method 300 can include determining second seizure data and/or second side effect data from the second patient data. The processes of block 308 can be identical or generally similar to the processes described above with respect to block 304. For example, the second seizure data (e.g., data characterizing seizure events experienced by the patient during the second time period) and/or second side effect data (e.g., data characterizing side effects and/or functional level of the patient during the second time period) can be determined from eye movement data and/or other patient data types using statistical analysis, pattern recognition, and/or trained machine learning algorithms, as previously discussed.

At block 310, the method 300 can include generating a personalized dose-response profile for the patient, based on the first and second seizure data and/or the first and second side effect data. The personalized dose-response profile can characterize how the particular patient responds to a treatment regimen of interest (e.g., different dosages of a medication, different medication types, different treatment modalities), in terms of therapeutic efficacy (e.g., reduction in seizure burden) and/or toxicity (e.g., increase in side effects severity). For example, the dose-response profile can include (1) a therapeutic dose-response profile characterizing therapeutic efficacy (e.g., change in seizure burden) with changes in treatment, and/or (2) a toxicity dose-response profile characterizing toxicity (e.g., change in side effects severity) with changes in treatment. The dose-response profile can optionally include a natural history curve showing changes to the patient's baseline (e.g., worsening cognition despite treatment changes). As previously discussed, the therapeutic efficacy and/or toxicity produced by a particular treatment can vary significantly from patient to patient. Additionally, the patient's neurocognitive function can be affected by the underlying disease or condition, as well as by the prescribed treatment. Accordingly, the personalized dose-response profile can provide a more accurate and reliable measure for assessing how well a specific patient is responding to treatment as it relates to their baseline and/or natural history.

The dose-response profile can be generated using various techniques. For example, the patient's therapeutic profile can be determined by comparing the second seizure data of block 308 to the first seizure data of block 304 to determine a change in seizure burden. As previously discussed, the first seizure data can represent the patient's baseline seizure burden (e.g., seizure burden before treatment has started or with an initial dosage of medication), and the second seizure data can represent the patient's seizure burden with a treatment of interest (e.g., seizure burden after treatment has started or with a different dosage of medication). The therapeutic efficacy for that particular treatment can be assessed based on how the seizure burden changes, e.g., a decrease in seizure burden can indicate that the treatment is effective, while an increase or no change in seizure burden can indicate that the treatment is ineffective or even harmful.

Similarly, the patient's toxicity profile can be determined by comparing the second side effect data of block 308 to the first side effect data of block 304 to determine a change in side effects severity. As previously discussed, the first side effect data can represent the patient's baseline function (e.g., functional level before treatment has started or with an initial dosage of medication), and the second side effect data can represent the patient's function with a treatment of interest (e.g., functional level after treatment has started or with a different dosage of medication). The toxicity for that particular treatment can be assessed based on how the side effects severity changes, e.g., a decrease or no change in side effects and/or improvement or no change in functioning can indicate that the treatment is less toxic or nontoxic, while an increase in side effects and/or reduction in functioning can indicate that the treatment is toxic. Additionally, the extent of toxicity can be evaluated by the magnitude of the change, e.g., a small increase in side effects and/or small reduction in functioning may be acceptable, while a large increase in side effects and/or large reduction in functioning may indicate unacceptable toxicity.

In embodiments where the first and second side effect data include data for two or more different types of side effects (e.g., drowsiness and processing speed), the method 300 can include generating a separate toxicity profile for each side effect, so that the effect of treatment on each side effect can be assessed separately. Alternatively or in combination, the method 300 can include generating an aggregated toxicity profile that represents the combined severity of all side effects. In such embodiments, the aggregated toxicity profile can be a weighted combination (e.g., weighted average) of the individual toxicity profile for each side effect type. The weight parameter for each side effect type can be determined in various ways, e.g., side effects that are less tolerable and/or more harmful can be weighted more heavily, side effects that change more significantly with treatment for a particular patient can be weighted more heavily, etc. In some embodiments, the weight parameters are determined using statistical analysis of previous patient data (e.g., from the same patient and/or from different patients) and/or machine learning techniques, e.g., side effects that are likely to have more predictive value and/or are more sensitive can be weighted more heavily.

In some embodiments, the personalized dose-response profile is generated by (1) producing a predicted dose-response profile for the patient, then (2) modifying the predicted dose-profile based on the seizure data and/or side effect data for that particular patient so as to produce a patient-specific version of the dose-response profile. In such embodiments, the predicted dose-response profile can be produced based on data from other patients, such as patients having similar characteristics as the patient of interest (e.g., with respect to age, gender, diagnosis, medical history, genotype, EEG abnormalities, treatment plan, etc.). For example, dose-response profiles for similar patients can be aggregated, averaged, or otherwise used to predict how the patient of interest will respond to treatment. Optionally, the predicted dose-response profile can be generated using a machine learning algorithm that is trained on dose-response profiles from multiple patients. The machine learning algorithm can receive patient data as input (e.g., information on the characteristics of a patient of interest), and generate a predicted dose-response profile for the patient as output. Subsequently, the predicted dose-response profile can be updated as actual seizure data and/or side effect data for the patient is received. This approach can allow the healthcare provider to predict how the patient will respond to treatment, even at earlier stages in the process when relatively little monitoring data is available.

Although FIG. 3 illustrates generating a personalized dose-response profile based on data from two time periods (e.g., a baseline time period and a treatment time period), in other embodiments, the data collection and analysis processes of the method 300 can be repeated multiple times so that the personalized dose-response profile is generated based on data from three, four, five, tens, hundreds, or thousands of time periods. For example, in some embodiments, the method 300 includes receiving third patient data for a third time period (e.g., a subsequent treatment time period), determining third seizure data and/or third side effect data from the third patient data, and generating the personalized dose-response profile using the third seizure data and/or third side effect data, and so on. In some embodiments, some or all of the time periods can be associated with a different dosage of the treatment (e.g., a different medication dosage according to a prescribed titration schedule), such that the personalized dose-response profile represents the patient's response to a plurality of different dosages (e.g., at least two, three, four, five, ten, or more different dosages). This approach can be used to build out titration curves showing how efficacy and/or toxicity change as a function of dosage. Alternatively or in combination, some or all of the time periods can be associated with different types and/or combinations of treatments (e.g., different medication combinations), so that the personalized dose-response profile can be used to compare the therapeutic and/or toxic effects of different treatments on the patient. Optionally, the patient may remain on the same treatment regimen during some or all of the time periods (e.g., on a maintenance dosage of medication), such that the personalized dose-response profile monitors the patient's response to that treatment regimen over an extended duration (e.g., at least 1 month, two months, 3 months, 6 months, 1 year, 2 years, 5 years, or more). This approach can be used to track long-term trends such as medication adherence, long-term side effects, and/or changes in therapeutic response (e.g., onset of a medication refractory state).

Optionally, the method 300 can further include outputting the personalized dose-response profile for review by a user (e.g., a healthcare professional such as a neurologist, the patient, a caregiver). The dose-response profile can be provided in various formats, such as graphs or other visual representations, a table or other structured data format, a textual summary, or suitable combinations thereof. As previously discussed, the personalized dose-response profile can be output as part of a report that is periodically transmitted to the healthcare professional for monitoring and managing the patient's care. For example, the personalized dose-response profile can be sent to the healthcare professional as one or more titration curves that correlate seizure control and/or side effects severity to treatment dosage. The healthcare professional can review various characteristics of the titration curves (e.g., the amplitude of the therapeutic curve versus the toxicity curve, the separation between the curves) to define and/or adjust the treatment plan. For example, in some embodiments, an ideal dose-response profile shows significant efficacy with minimal side effects and excellent patient reported tolerability as the dosage increases. Dose-response profiles showing poor effectiveness, severe side effects, and/or poor patient-reported tolerability can indicate that a different treatment regimen should be tried. Such information may be difficult to obtain using conventional techniques, thus resulting in overtreating (e.g., high dosages without significant benefits) or undertreating (e.g., not prescribing sufficient treatment to achieve seizure freedom).

At block 312, the method 300 can optionally include generating a treatment recommendation for the patient, based on the personalized dose-response profile of block 310. For example, the treatment recommendation can include any of the following: increasing a dosage of a medication, decreasing a dosage of a medication, starting a medication, stopping a medication, changing to a different medication, combining two or more medications, combining a medication with another treatment modality, determining that the patient is refractory to medication, altering a neurostimulation parameter (e.g., frequency, amplitude, duration, stimulation location), starting neurostimulation, stopping neurostimulation, changing the patient's diet, and/or referring the patient for surgery. As previously discussed, the treatment recommendation can be output to the healthcare professional, patient, caregiver, and/or other user as part of the report and/or as a separate notification.

In some embodiments, the treatment recommendation is generated automatically using techniques such as statistical analysis, pattern recognition, and/or machine learning. For example, the method 300 can include identifying other patients that have similar personalized dose-response profiles as the patient of interest, retrieving previous patient data characterizing how those similar patients responded to treatment, and recommending a treatment plan for the patient of interest based on the previous patient data. Alternatively or in combination, the method 300 can include inputting the personalized dose-response profile into a trained machine learning algorithm that has been trained on dose-response data and treatment plan data from a plurality of different patients. The machine learning algorithm can output a prediction of whether a particular treatment will be effective and/or toxic for the patient, recommend treatments, predict effects of changes to treatment, etc.

Figure 7:
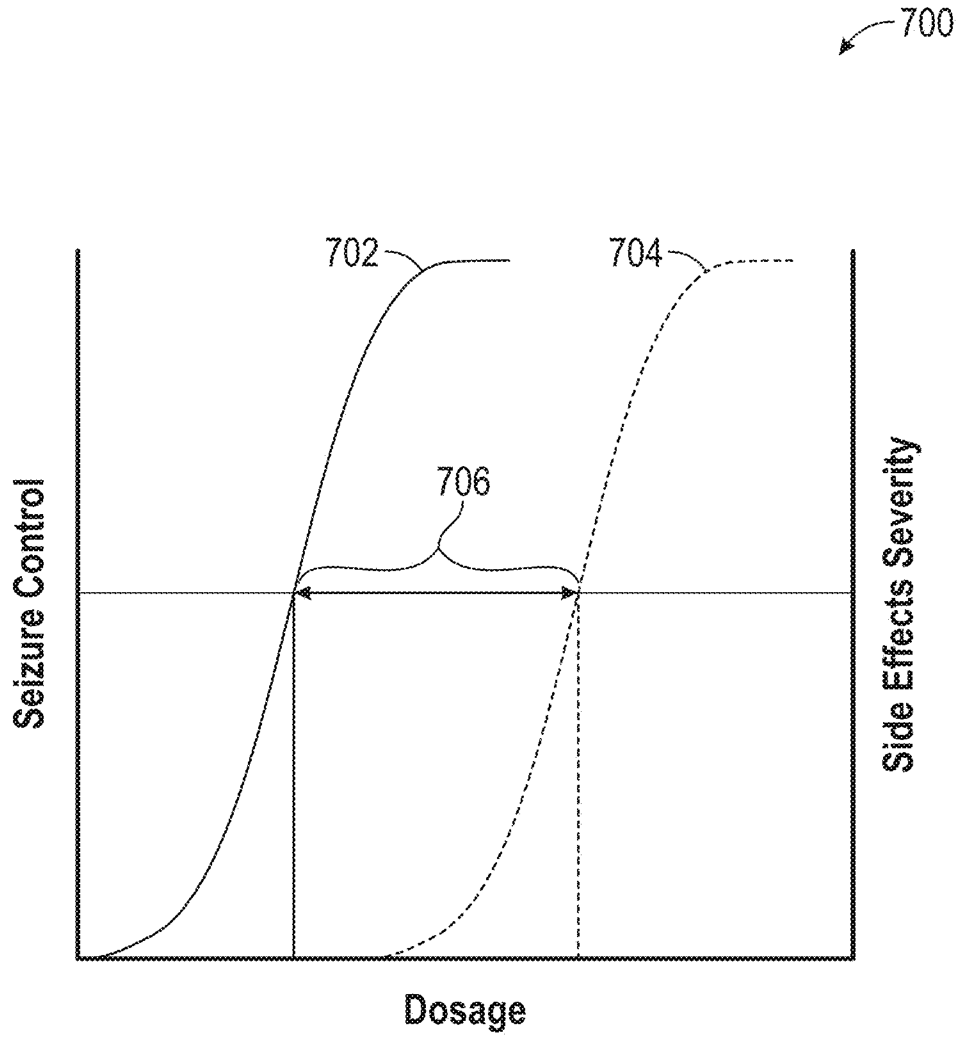
FIG. 7 is a graph illustrating an example of a personalized dose-response profile, in accordance with embodiments of the present technology.

FIG. 7 is a graph illustrating a representative example of a personalized dose-response profile 700, in accordance with embodiments of the present technology. The dose-response profile includes a therapeutic profile 702 and a toxicity profile 704 for a particular patient. The curve representing the therapeutic profile 702 plots seizure control as a function of treatment dosage (e.g., medication dosage, neurostimulation dosage). Higher seizure control correlates to reduced seizure burden, and can be measured as a percentage decrease in seizure counts, duration, and/or severity relative to a baseline (e.g., when the patient is not taking any medication). The curve representing the toxicity profile 704 plots severity of side effects as a function of dosage, and can be measured as a percentage increase in seizure rate, drowsiness, slowed processing speed, and/or other functional impairment relative to a baseline (e.g., when the patient is not taking any medication). The therapeutic profile 702 and toxicity profile 704 can be used to determine the therapeutic index 706 of the treatment, which is a ratio of the dosage that produces a toxic effect (e.g., 50% side effects severity) to the dosage that produces a therapeutic effect (e.g., 50% seizure control). A higher therapeutic index 706 can indicate that the treatment is relatively safe, because the dosage that produces a toxic effect is significantly higher than the dosage that produces a therapeutic effect. Conversely, a lower therapeutic index 706 can indicate that the treatment is less safe, because the dosage needed to produce a therapeutic effect is closer to the dosage that results in toxicity. In some embodiments, a healthcare professional can compare the amplitude of the therapeutic profile 702 (representing the efficacy of the treatment) to the therapeutic index 706 to evaluate the patient's condition and/or recommend corrective action with therapeutics.

Figure 8A:
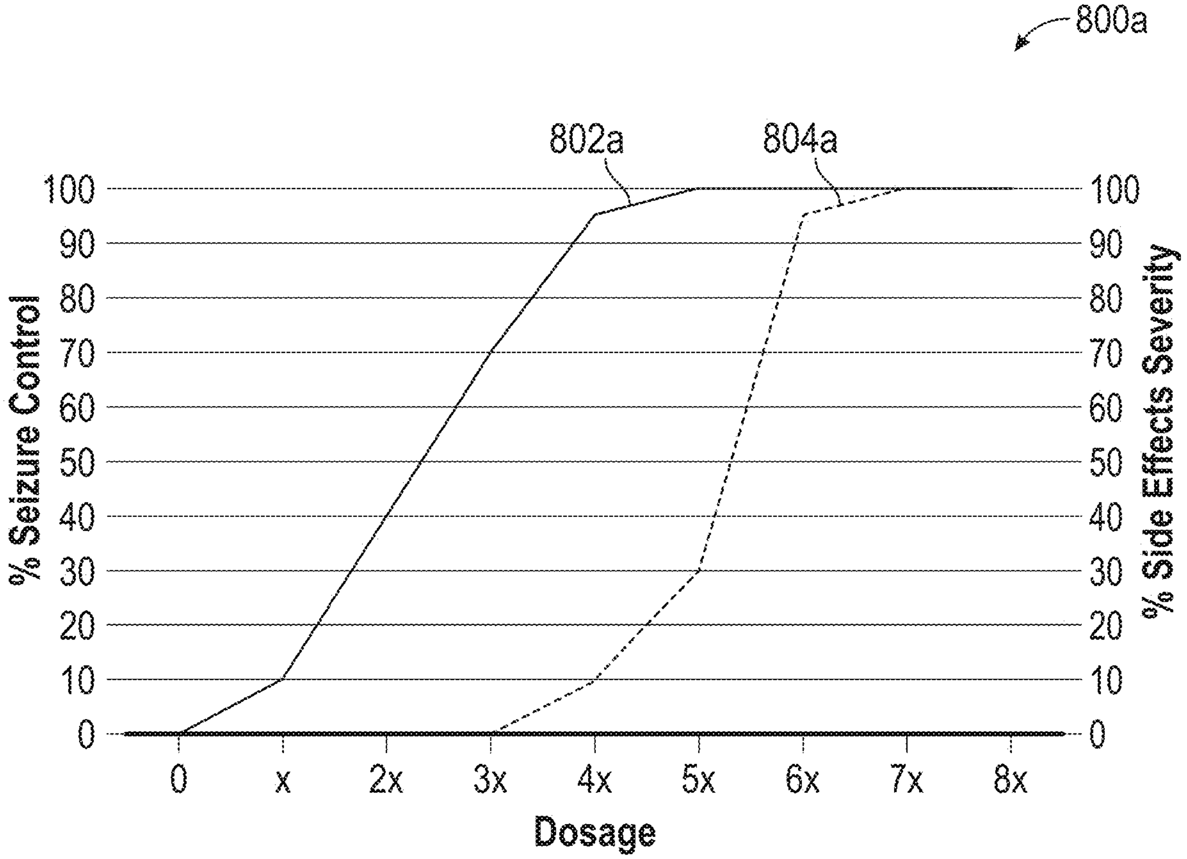
FIGS. 8A-8D are graphs illustrating additional examples of personalized dose-response profiles, in accordance with embodiments of the present technology.

FIGS. 8A-8D are graphs illustrating additional examples of personalized dose-response profiles 800*a*-800*d* that can be generated in accordance with embodiments of the present technology. Referring first to FIG. 8A, the dose-response profile 800*a* shows that the treatment is effective (e.g., the therapeutic profile 802*a* has a large amplitude with a maximum value of 100% seizure control) but includes moderate side effects (e.g., the toxicity profile 804*a* also has a large amplitude, but is horizontally separated from the therapeutic profile 802*a* so that the side effects severity is approximately 30% at the 100% effective dosage). Accordingly, the healthcare professional may recommend that the patient continue the treatment but keep the dosage relatively low.

Figure 8B:
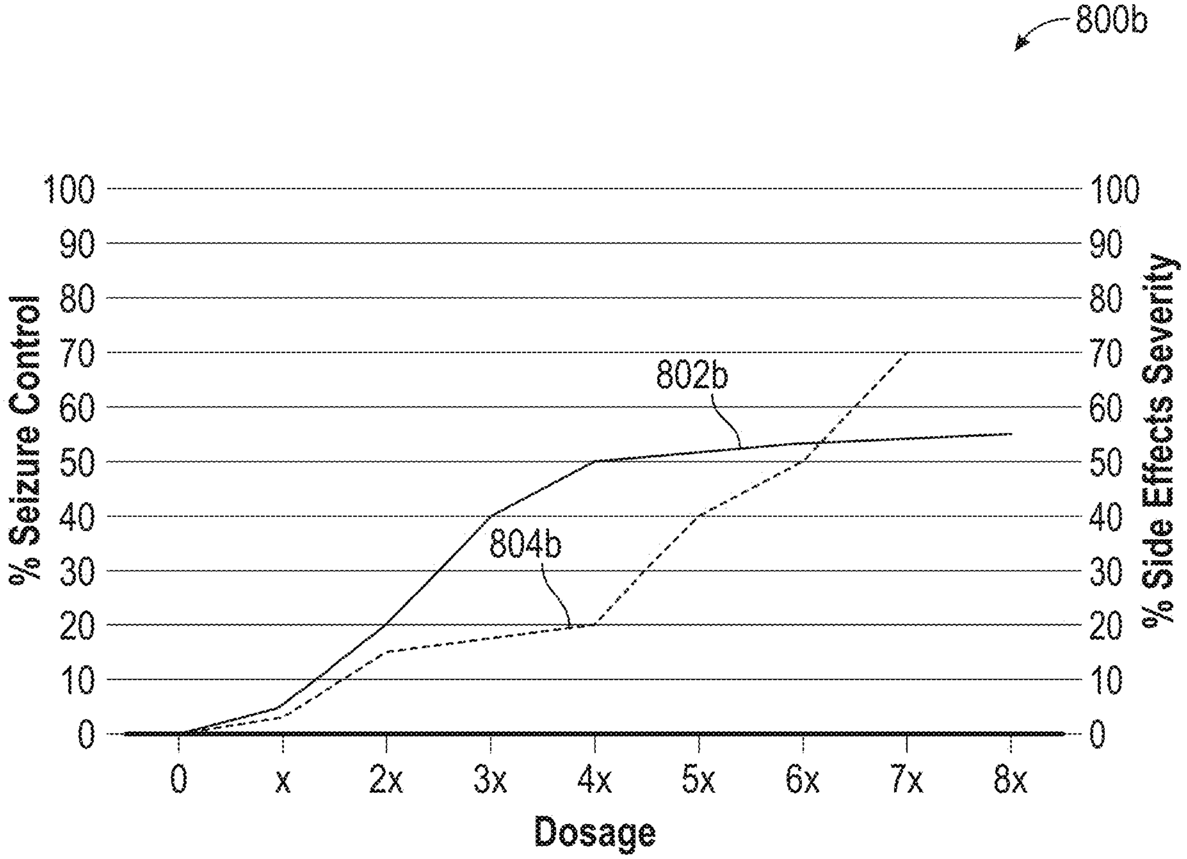

Referring next to FIG. 8B, the dose-response profile 800*b* shows that the treatment has poor efficacy (e.g., the therapeutic profile 802*b* has a small amplitude with a maximum value of 55% seizure control) and includes moderate side effects (e.g., the toxicity profile 804*b* overlaps the therapeutic profile 802*b* within the effective dosage range). Thus, the healthcare professional may recommend that the patient stop this particular treatment.

Figure 8C:
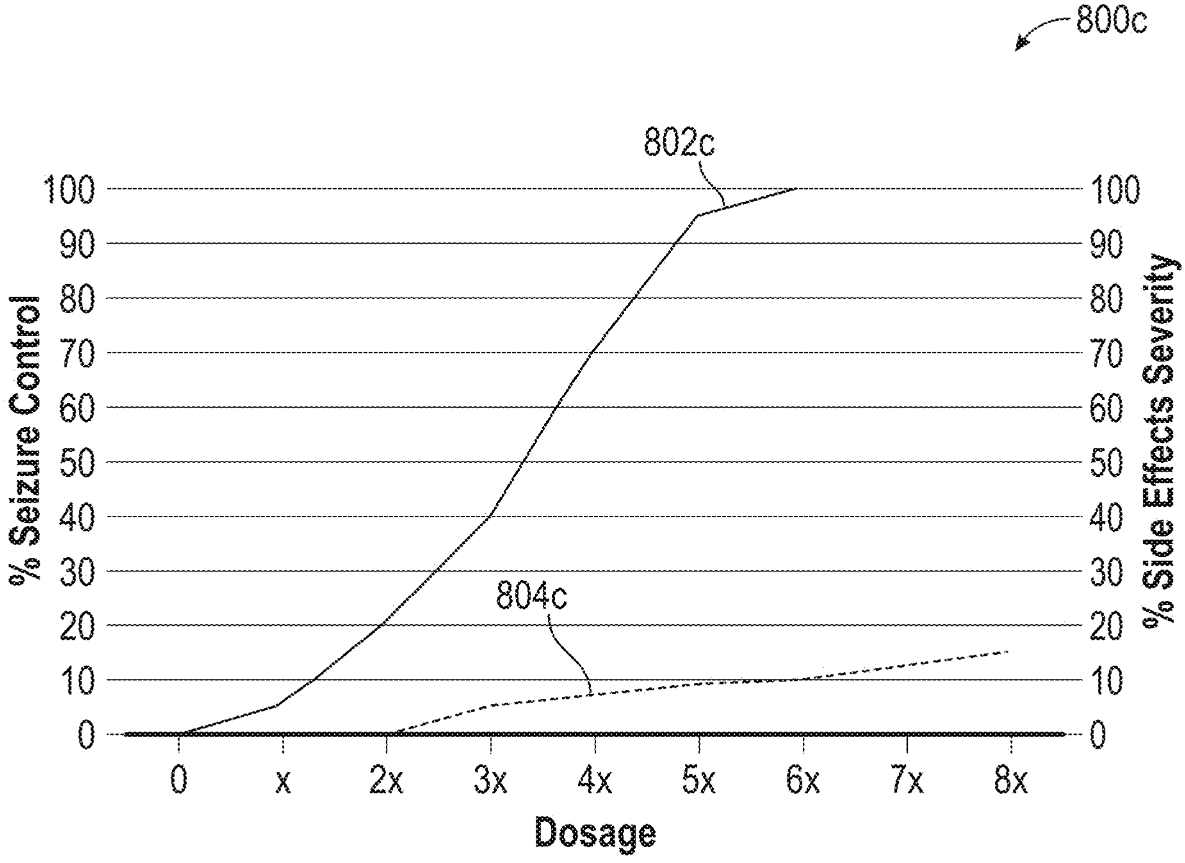

Referring next to FIG. 8C, the dose-response profile 800*c* shows that the treatment is effective (e.g., the therapeutic profile 802*c* has a large amplitude with a maximum value of 100% seizure control) and has minor side effects (e.g., the toxicity profile 804*c* has a small amplitude so that the side effects severity is less than 20% at the 100% effective dosage). In this case, the healthcare professional may recommend that the patient continue the treatment with higher dosages.

Figure 8D:
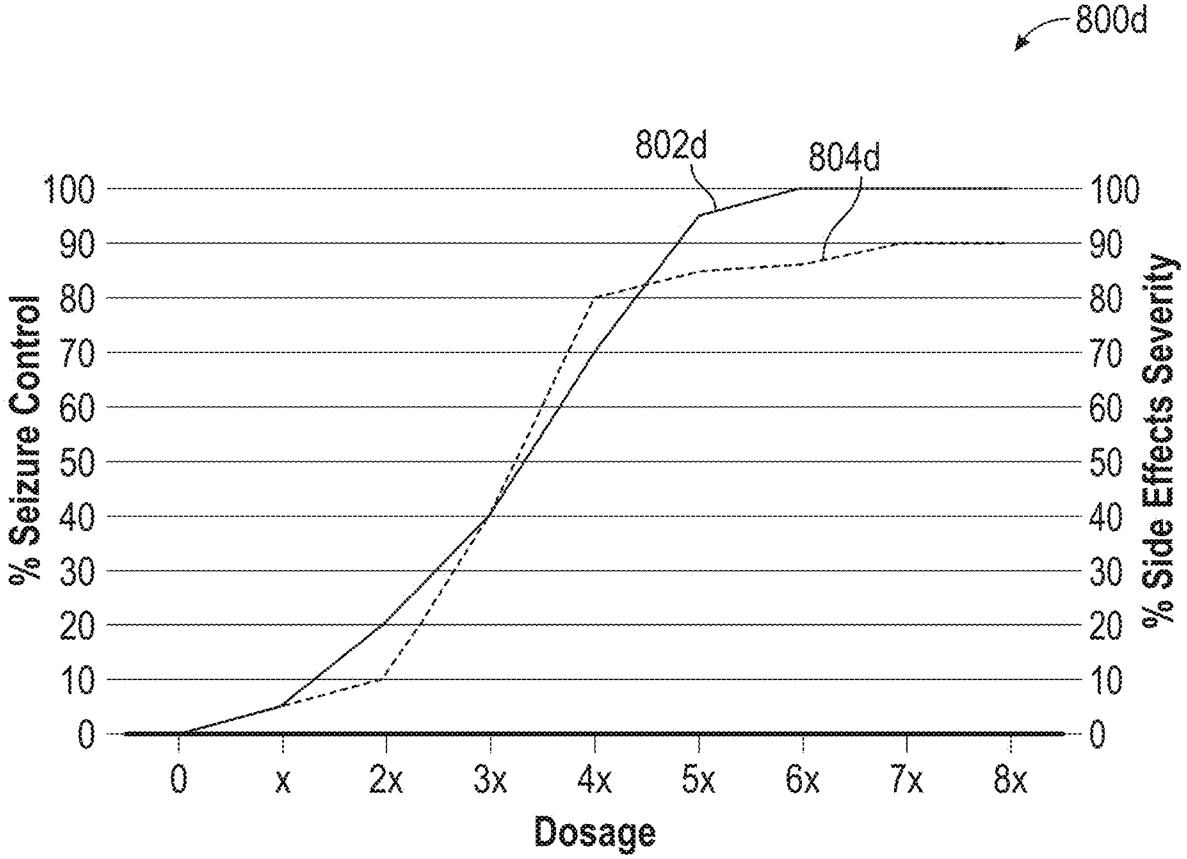

Referring next to FIG. 8D, the dose-response profile 800*d* shows that the treatment is effective (e.g., the therapeutic profile 802*d* has a large amplitude with a maximum value of 100% seizure control) but the patient is experiencing severe side effects (e.g., the toxicity profile 804*d* has a large amplitude and overlaps the therapeutic profile 802*d* throughout the dosage range). Accordingly, the healthcare professional may recommend that the patient stop this particular treatment.

In some embodiments, once a maintenance dosage of the treatment has been determined, the techniques described herein can be used to track the patient's dose-response profile over extended time periods (e.g., weeks, months, years) to identify the emergence of drug resistance (e.g., refractory epilepsy), changes in side effects severity, and/or other longer-term effects. For example, as multiple therapies are titrated over time, side effects could be cumulative or not increase significantly. Additionally, extended monitoring can also be used to track patient compliance with treatment.

Figure 9A:
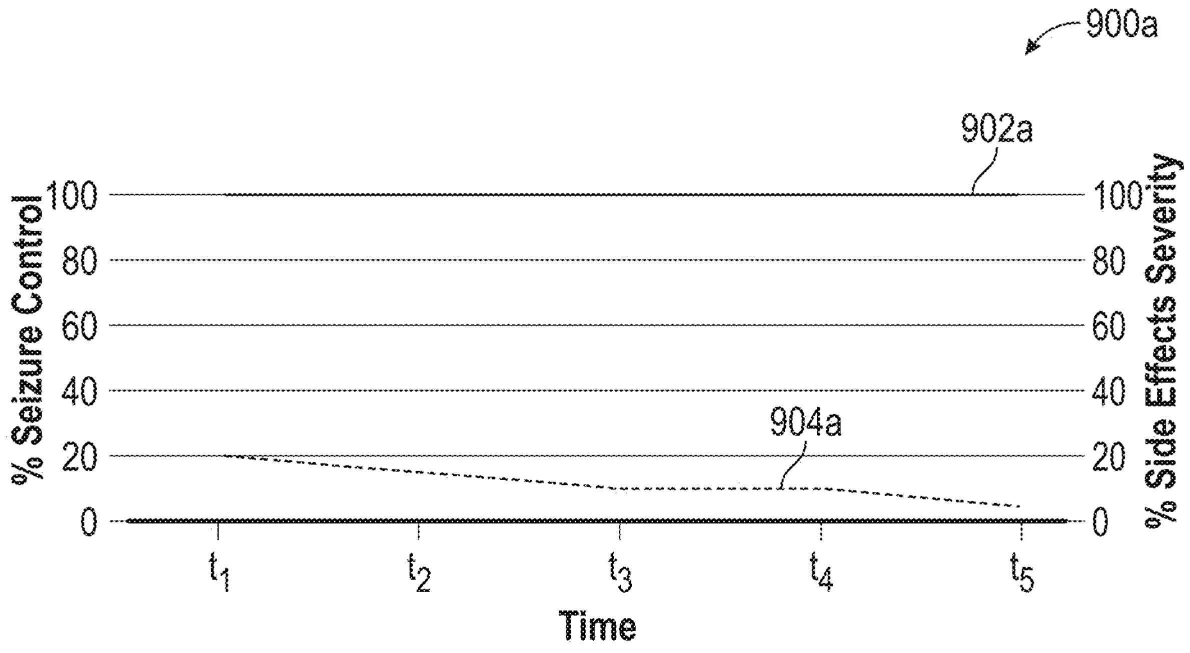
FIGS. 9A-9D are graphs illustrating further examples of personalized dose-response profiles, in accordance with embodiments of the present technology.

FIGS. 9A-9D are graphs illustrating representative examples of personalized dose-response profiles 900*a*-900*d* that can be generated in accordance with embodiments of the present technology. Referring first to FIG. 9A, the dose-response profile 900*a* shows that the maintenance dosage is very effective (e.g., the therapeutic profile 902*a* shows 100% seizure control over time), with improving side effects (e.g., the toxicity profile 904*a* shows low and decreasing side effects severity over time). Accordingly, the healthcare professional may recommend that the patient continue the treatment at the current dosage.

Figure 9B:
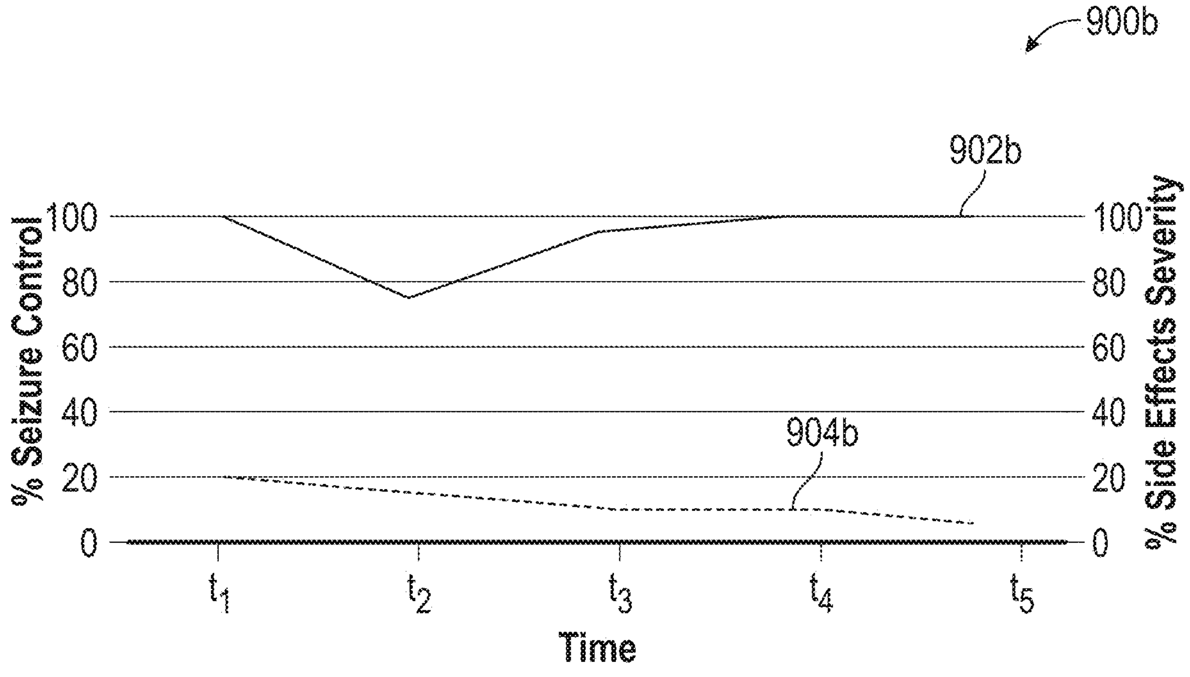

Referring next to FIG. 9B, the dose-response profile 900*b* shows a temporary reduction in efficacy as evidenced by a slight decrease in the therapeutic profile 902*b* at time $t_2$. This may indicate that the patient temporarily stopped treatment (e.g., missed medication dosage). Since the treatment otherwise appears to be effective (e.g., seizure control is approximately 100%) with improving side effects (e.g., the toxicity profile 904*a* shows low and decreasing side effects severity over time), the healthcare professional may recommend that the patient continue the treatment at the current dosage, but take steps to improve their adherence to the therapeutic regimen.

Figure 9C:
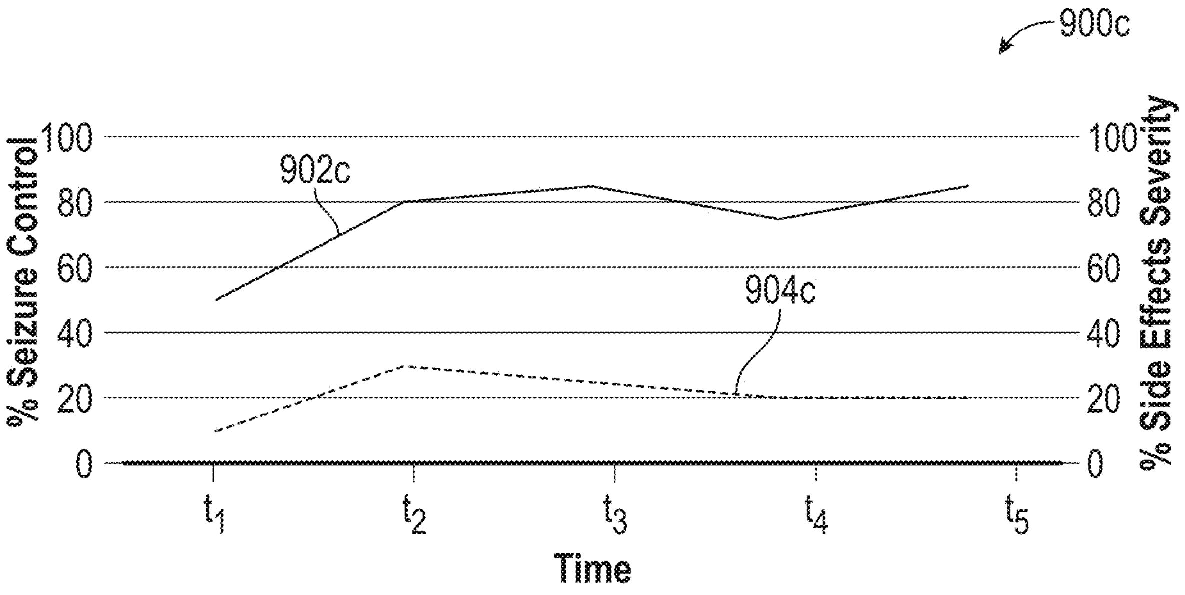

Referring next to FIG. 9C, the dose-response profile 900*c* shows that addition of a second treatment (e.g., a second medication) at time $t_2$ produced a moderate improvement in seizure control compared to the initial treatment alone (e.g., as indicated by the slight increase in the therapeutic profile 902*c*). Although there was an initial increase in side effects severity when the second treatment was introduced (e.g., as indicated by the temporary increase in the toxicity profile 904*c* at time $t_2$), the side effects improved over time. Thus, the healthcare professional may recommend that the patient continue with both treatments.

Figure 9D:
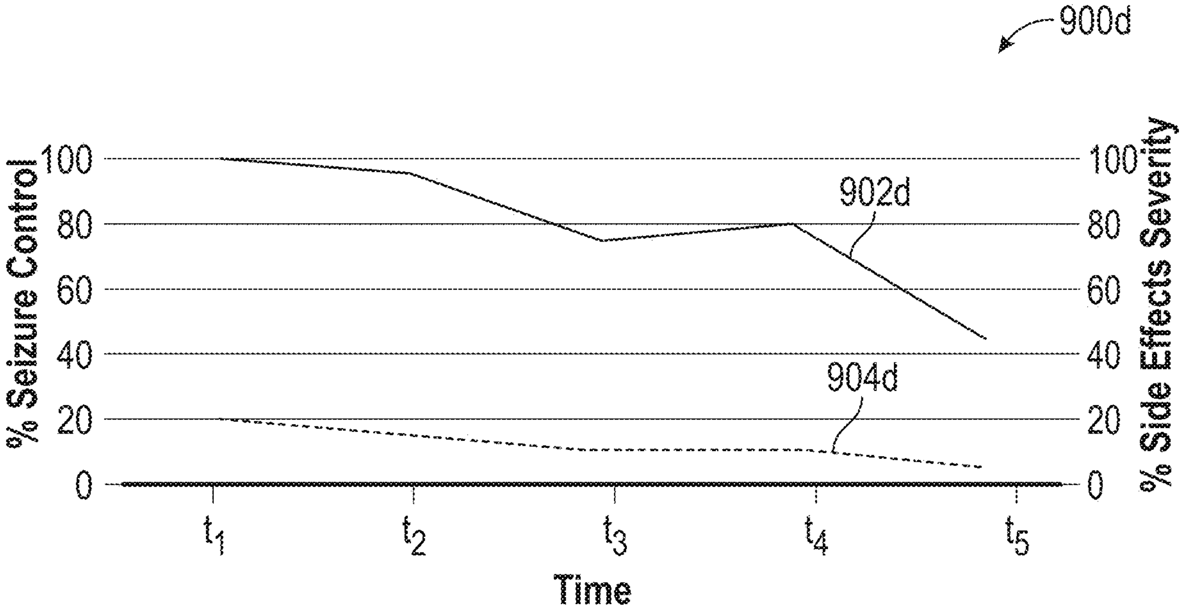

Referring next to FIG. 9D, the dose-response profile 900*d* shows that the initial treatment is losing efficacy over time, and that the addition of a second treatment at time $t_3$ did not improve the patient's therapeutic response (e.g., as indicated by the decreasing therapeutic profile 902*d* over time), even though the patient experienced only minor side effects (e.g., as indicated by the consistently low toxicity profile 904*d*). Accordingly, the healthcare professional may conclude that the patient is exhibiting refractory epilepsy and may refer the patient to a different treatment modality altogether.

Referring again to FIG. 3, the method 300 can be modified in many different ways. For example, in some embodiments, the method 300 is not limited to monitoring spontaneous seizure events, and can alternatively or additionally include inducing seizure events using hyperventilation, startling, sleep deprivation, cognitive stress, photic stimulation, and/or other techniques known to those of skill in the art. For example, seizure events can be induced using the embodiments described in U.S. Provisional Application No. 63/239,158, the disclosure of which is incorporated by reference herein in its entirety. The characteristics of the induced seizure can be monitored using any of the techniques and devices described above, and can subsequently be used to characterize therapeutic efficacy. For example, changes in the threshold for causing induced seizures and/or the severity of induced seizures can be used to assess whether a particular treatment is effective for improving seizure control. Additionally, some or all of the processes of the method 300 can be performed multiple times to monitor the patient over time, and/or to continuously or periodically update the dose-response profile and/or treatment recommendations. Optionally, some or all of the processes of the method 300 can be omitted, such as the process of block 312.

EXAMPLES

The following examples are included to further describe some aspects of the present technology, and should not be used to limit the scope of the technology.

1. A computer-implemented method for monitoring a patient having a neurological disease or condition, the method comprising:

receiving, from one or more patient monitoring devices, first patient data for a baseline time period;

determining, based on the first patient data, first seizure data and first side effect data during the baseline time period;

receiving, from the one or more patient monitoring devices, second patient data for a treatment time period;

determining, based on the second patient data, second seizure data and second side effect data during the treatment time period; and generating a personalized dose-response profile for the patient based on the first and second seizure data and the first and second side effect data.

2. The computer-implemented method of Example 1, wherein the neurological disease or condition comprises epilepsy or a disorder having epilepsy as a symptom.

3. The computer-implemented method of Example 2, wherein the epilepsy comprises absence epilepsy.

4. The computer-implemented method of any one of Examples 1 to 3, wherein the one or more patient monitoring devices comprise an eye tracking device, and the first and second patient data comprise eye movement data produced by the eye tracking device.

5. The computer-implemented method of Example 4, wherein the eye movement data includes one or more of the following: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, eye rolling, jerky eye movements, saccadic velocity, saccadic direction, torsional velocity, torsional direction, gaze direction, gaze scanning patterns, or eye activity during sleep.

6. The computer-implemented method of any one of Examples 1 to 5, wherein the one or more patient monitoring devices comprise a facial tracking device, and the first and second patient data comprise facial movement data produced by the facial tracking device.

7. The computer-implemented method of Example 6, wherein the facial movement data includes a change in one or more of the following: distance between the patient's eyes, distance between the patient's eyelids, width of the patient's nose, center of the patient's nose, depth of the patient's eye sockets, shape of the patient's cheekbones, length of the patient's jawline, distance between the patient's mouth edges center of the patient's mouth, or focal weakness.

8. The computer-implemented method of any one of Examples 1 to 7, wherein the one or more patient monitoring devices comprise one or more of the following: a brain monitoring device, a mobile device, an implantable device, a wearable device, or a computing device.

9. The computer-implemented method of any one of Examples 1 to 8, further comprising receiving additional patient data, wherein one or more of the first seizure data, first side effect data, second seizure data, or second side effect data are determined based on the additional patient data.

10. The computer-implemented method of Example 9, wherein the additional patient data comprises one or more of the following: neuropsychological assessment data, self-reporting data, or electronic health record data.

11. The computer-implemented method of any one of Examples 1 to 10, wherein the first and second seizure data include data representing one or more of a type, a timing, an ictal duration, a postictal duration, a frequency, a severity, or a variability of at least one seizure event experienced by the patient.

12. The computer-implemented method of Example 11, wherein the at least one seizure event comprises one or more of the following: an absence seizure, an atypical absence seizure, a tonic-clonic seizure, a clonic seizure, a tonic seizure, an atonic seizure, a myoclonic seizure, a simple partial seizure, a complex partial seizure, a secondary generalized seizure, or an infantile spasm.

13. The computer-implemented method of any one of Examples 1 to 12, further comprising comparing the first and second seizure data to determine a change in seizure burden between the baseline time period and the treatment time period.

14. The computer-implemented method of any one of Examples 1 to 13, wherein the first and second side effect data include data representing one or more of a type, a timing, a duration, a frequency, or a severity of at least one side effect experienced by the patient.

15. The computer-implemented method of Example 14, wherein the at least side effect comprises one or more of the following: drowsiness, a decrease in cognition, a decrease in attention, a decrease in concentration, a change in mood, a change in behavior, loss of consciousness, suicidality, homicidality, irritability, or a change in vision.

16. The computer-implemented method of any one of Examples 1 to 15, further comprising comparing the first and second side effect data to determine a change in side effect severity between the baseline time period and the treatment time period.

17. The computer-implemented method of any one of Examples 1 to 16, wherein:

the first and second seizure data are determined from the first and second patient data using a first set of algorithms, and the first and second side effect data are determined from the first and second patient data using a second set of algorithms.

18. The computer-implemented method of Example 17, wherein the first set of algorithms includes at least one machine learning algorithm trained on seizure data from a plurality of patients.

19. The computer-implemented method of Example 17 or 18, wherein the second set of algorithms includes at least one machine learning algorithm trained on interictal data from a plurality of patients.

20. The computer-implemented method of any one of Examples 1 to 19, wherein the baseline time period occurs before the patient has started a treatment for the neurological disease or condition, and the treatment time period occurs after the patient has started the treatment for the neurological disease or condition.

21. The computer-implemented method of Example 20, wherein the treatment comprises at least one medication.
22. the Computer-implemented Method of Example 20 or 21, Wherein the treatment comprises neurostimulation.
23. The computer-implemented method of any one of Examples 1 to 19, wherein the baseline time period occurs while the patient is taking a first dosage of a medication for the neurological disease or condition, and the treatment time period occurs while the patient is taking a second dosage of the medication for the neurological disease or condition.
24. The computer-implemented method of any one of Examples 1 to 23, further comprising:
receiving, from the one or more patient monitoring devices, third patient data for a subsequent treatment time period, and
determining, based on the third patient data, third seizure data and third side effect data during the subsequent treatment time period,
wherein the personalized dose-response profile for the patient is generated based on the third seizure data and the third side effect data.
25. The computer-implemented method of Example 24, wherein:
the baseline time period occurs before the patient has started taking a medication for the neurological disease or condition,
the treatment time period occurs while the patient is taking a first dosage of the medication, and
the subsequent treatment time period occurs while the patient is taking a second dosage of the medication.
26. The computer-implemented method of any one of Examples 1 to 25, wherein the personalized dose-response profile comprises a therapeutic profile representing a relationship between seizure control and medication dosage for the patient.
27. The computer-implemented method of any one of Examples 1 to 26, wherein the personalized dose-response profile comprises a toxicity profile representing a relationship between side effect severity and medication dosage for the patient.
28. The computer-implemented method of any one of Examples 1 to 27, wherein generating the personalized dose-response profile comprises:
generating a predicted dose-response profile for the patient, and
modifying the predicted dose-response profile based on the first and second seizure data and the first and second side effect data to generate the personalized dose-response profile.
29. The computer-implemented method of Example 28, wherein the predicted dose-response profile is generated based on dose-response profiles from a plurality of patients having similar characteristics as the patient.
30. The computer-implemented method of Example 28 or 29, wherein the predicted dose-response profile is generated using a machine learning algorithm trained on seizure data and side effect data from a plurality of patients.
31. The computer-implemented method of any one of Examples 1 to 30, further comprising providing a treatment recommendation for the patient, based on the personalized dose-response profile.
32. The computer-implemented method of Example 31, wherein the treatment recommendation comprises one or more of the following: increasing a dosage of a medication, decreasing a dosage of a medication, starting a medication, stopping a medication, changing to a different medication, combining two or more medications, combining a medication with another treatment modality, determining that the patient is refractory to medication, altering a neurostimulation parameter, starting neurostimulation, stopping neurostimulation, or changing the patient's diet.
33. The computer-implemented method of Example 31 or 32, wherein the treatment recommendation is determined based on data from a plurality of patients having similar personalized dose-response profiles as the patient.
34. The computer-implemented method of any one of Examples 31 to 33, wherein the treatment recommendation is determined using a machine learning algorithm trained on dose-response profiles from a plurality of patients.
35. A computer-implemented method for managing epilepsy, the method comprising:
receiving, from an eye tracking device, first eye movement data of a patient during a baseline period before the patient has started taking a medication for the epilepsy;
determining, based on the first eye movement data, first seizure burden data and first neurocognitive data for the patient during the baseline period;
receiving, from the eye tracking device, second eye movement data of the patient during a treatment period in which the patient is taking the medication;
determining, based on the second eye movement data, second seizure burden data and second neurocognitive data for the patient during the treatment period;
generating a personalized dose-response profile for the patient based on the first and second seizure burden data and the first and second neurocognitive data; and
outputting a treatment recommendation for the patient based on the personalized dose-response profile.
36. A system for monitoring a patient having a neurological disease or condition, the system comprising:
one or more processors; and
a memory operably coupled to the one or more processors and storing instructions that, when executed by the processor, cause the system to perform operations comprising:
receiving baseline patient data from at least one patient monitoring device associated with the patient,
determining, using the baseline patient data, first seizure data and first side effect data for the patient,
receiving treatment patient data from the at least one patient monitoring device associated with the patient,
determining, using the treatment patient data, second seizure data and second side effect data for the patient, and
generating a patient-specific dose-response profile based on the first and second seizure data and the first and second side effect data.
37. The system of Example 36, wherein the neurological disease or condition comprises epilepsy or a disorder having epilepsy as a symptom.
38 The system of Example 36 or 37, wherein the at least one patient monitoring device comprises an eye tracking device, and the baseline patient data and the treatment patient data comprise eye movement data produced by the eye tracking device.
39. The system of Example 38, wherein the eye movement data includes one or more of the following: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, eye rolling, jerky eye movements, saccadic velocity, saccadic direction, torsional velocity, torsional direction, gaze direction, gaze scanning patterns, or eye activity during sleep.

40. The system of Example 38 or 39, wherein the eye tracking device is a wearable device.

41. The system of any one of Examples 38 to 40, wherein the eye tracking device is an electrooculography-based device.

42. The system of any one of Examples 38 to 40, wherein the eye tracking device is a video-based device.

43. The system of any one of Examples 38 to 42, wherein the eye tracking device is operably coupled to a computing device, and the baseline patient data and the treatment data are transmitted from the eye tracking device to the system via the computing device.

44. The system of any one of Examples 36 to 43, wherein the at least one patient monitoring device comprises a facial tracking device, and the baseline patient data and the treatment patient data comprise facial movement data produced by the facial tracking device.

45. The system of Example 44, wherein the facial movement data includes a change in one or more of the following: distance between the patient's eyes, distance between the patient's eyelids, width of the patient's nose, center of the patient's nose, depth of the patient's eye sockets, shape of the patient's cheekbones, length of the patient's jawline, distance between the patient's mouth edges center of the patient's mouth, or focal weakness.

46. The system of Example 44 or 45, wherein the facial tracking device is a video-based device or an electrooculography-based device.

47. The system of any one of Examples 36 to 46, wherein the at least one patient monitoring device comprises a single device configured to produce eye movement data and facial movement data.

48. The system of any one of Examples 36 to 47, wherein the at least one patient monitoring device comprises two or more different devices.

49. The system of any one of Examples 36 to 48, wherein the at least one patient monitoring device comprises one or more of the following: one or more of the following: a brain monitoring device, a mobile device, an implantable device, a wearable device, or a computing device.

50. The system of any one of Examples 36 to 49, wherein the operations further comprise receiving additional patient data, wherein one or more of the first seizure data, first side effect data, second seizure data, or second side effect data are determined based on the additional patient data.

51. The system of Example 50, wherein the additional patient data comprises one or more of the following: neuropsychological assessment data, self-reporting data, or electronic health record data.

52. The system of any one of Examples 36 to 51, wherein the first and second seizure data include data representing one or more of a type, a timing, an ictal duration, a postictal duration, a frequency, a severity, or a variability of at least one seizure event experienced by the patient.

53. The system of any one of Examples 36 to 52, wherein the operations further comprise comparing the first and second seizure data to determine a change in seizure burden.

54. The system of any one of Examples 36 to 53, wherein the first and second side effect data include data representing one or more of a type, a timing, a duration, a frequency, or a severity of at least one side effect experienced by the patient.

55. The system of any one of Examples 36 to 54, wherein the operations further comprise comparing the first and second side effect data to determine a change in side effect severity.

56. The system of any one of Examples 36 to 55, wherein:

the first and second seizure data are determined from the baseline and treatment patient data using a first set of algorithms, and the first and second side effect data are determined from the baseline and treatment patient data using a second set of algorithms.

57. The system of Example 56, wherein the first set of algorithms includes at least one machine learning algorithm trained on seizure data from a plurality of patients.

58. The system of Example 56 or 57, wherein the second set of algorithms includes at least one machine learning algorithm trained on interictal data from a plurality of patients.

59. The system of any one of Examples 36 to 58, wherein the baseline patient data is produced before the patient has started a treatment for the neurological disease or condition, and the treatment patient data is produced after the patient has started the treatment for the neurological disease or condition.

60. The system of any one of Examples 36 to 58, wherein the baseline patient data is produced while the patient is taking a first dosage of a medication for the neurological disease or condition, and the treatment patient data is produced while the patient is taking a second dosage of the medication for the neurological disease or condition.

61. The system of any one of Examples 36 to 60, wherein the operations further comprise:

receiving additional treatment patient data from the at least one patient monitoring device associated with the patient, and determining, using the additional treatment patient data, third seizure data and third side effect data for the patient.

wherein the patient-specific dose-response profile is generated based on the third seizure data and the third side effect data.

62. The system of Example 61, wherein:

the baseline patient data is produced before the patient has started taking a medication for the neurological disease or condition, the treatment patient data is produced while the patient is taking a first dosage of the medication, and the additional treatment patient data is produced while the patient is taking a second dosage of the medication.

63. The system of any one of Examples 36 to 62, wherein the patient-specific dose response profile comprises a therapeutic profile representing a relationship between seizure control and treatment dosage for the patient.

64 The system of any one of Examples 36 to 63, wherein the patient-specific dose response profile comprises a toxicity profile representing a relationship between side effect severity and medication dosage for the patient.

65. The system of any one of Examples 36 to 64, wherein generating the patient-specific dose-response profile comprises:

generating a predicted dose-response profile for the patient, and modifying the predicted dose-response profile based on the first and second seizure data and the first and second side effect data to generate the patient-specific dose-response profile.

66 The system of Example 65, wherein the predicted dose-response profile is generated based on dose-response profiles from a plurality of patients having similar characteristics as the patient.

67. The system of Example 65 or 66, wherein the predicted dose-response profile is generated using a machine learning algorithm trained on seizure data and side effect data from a plurality of patients.

68. The system of any one of Examples 36 to 67, wherein the operations further comprise providing a treatment recommendation for the patient, based on the patient-specific dose-response profile.

69. The system of Example 68, wherein the treatment recommendation comprises one or more of the following: increasing a dosage of a medication, decreasing a dosage of a medication, starting a medication, stopping a medication, changing to a different medication, combining two or more medications, combining a medication with another treatment modality, determining that the patient is refractory to medication, altering a neurostimulation parameter, starting neurostimulation, stopping neurostimulation, or changing the patient's diet.

70. The system of Example 68 or 69, wherein the treatment recommendation is determined based on data from a plurality of patients having similar dose-response profiles as the patient.

71 The system of any one of Examples 68 to 70, wherein the treatment recommendation is determined using a machine learning algorithm trained on dose-response profiles from a plurality of patients.

72 A non-transitory computer-readable storage medium comprising instructions that, when executed by one or more processors of a computing system, cause the computing system to perform operations comprising:

determining, based on baseline data produced by at least one monitoring device associated with a patient, first seizure data and first neurocognitive data during a baseline time period;

determining, based on treatment data produced by the at least one monitoring device associated with the patient, second seizure data and second neurocognitive data during a treatment time period; and generating a personalized dose-response profile for the patient based on the first and second seizure data and the first and second neurocognitive data.

73. A computer-implemented method for monitoring a patient having a neurological disease or condition, the method comprising:

receiving, from an eye tracking device, first eye movement data for a baseline time period;

determining, based on the first eye movement data, first seizure data during the baseline time period;

receiving, from the eye tracking device, second eye movement data for a treatment time period;

determining, based on the second eye movement data, second seizure data during the treatment time period; and generating a therapeutic dose-response profile for the patient based on the first and second seizure data.

74. The computer-implemented method of Example 73, wherein the neurological disease or condition comprises epilepsy or a disorder having epilepsy as a symptom.

75. The computer-implemented method of Example 73 or 74, wherein the first and second eye movement data each include one or more of the following: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, eye rolling, jerky eye movements, saccadic velocity, saccadic direction, torsional velocity, torsional direction, gaze direction, gaze scanning patterns, or eye activity during sleep.

76. The computer-implemented method of any one of Examples 73 to 75, further comprising receiving additional data, wherein one or more of the first seizure data or the second seizure data are determined based on the additional data.

77. The computer-implemented method of Example 76, wherein the additional data is received from one or more of the following: a facial tracking device, a brain monitoring device, a mobile device, an implantable device, a wearable device, or a computing device.

78. The computer-implemented method of Example 76 or 77, wherein the additional data comprises one or more of the following: facial movement data, brain monitoring data, neuropsychological assessment data, self-reporting data, or electronic health record data.

79. The computer-implemented method of any one of Examples 73 to 78, wherein the first and second seizure data include data representing one or more of a type, a timing, an ictal duration, a postictal duration, a frequency, a severity, or a variability of at least one seizure event experienced by the patient.

80 The computer-implemented method of Example 79, wherein the at least one seizure event comprises one or more of the following: an absence seizure, an atypical absence seizure, a tonic-clonic seizure, a clonic seizure, a tonic seizure, an atonic seizure, a myoclonic seizure, a simple partial seizure, a complex partial seizure, a secondary generalized seizure, or an infantile spasm.

81. The computer-implemented method of any one of Examples 73 to 80, wherein the therapeutic dose-response profile represents a change in seizure burden between the baseline time period and the treatment time period.

82. The computer-implemented method of any one of Examples 73 to 81, further comprising:

determining, based on the first eye movement data, first side effect data during the baseline time period, determining, based on the second eye movement data, second side effect data during the treatment time period, and generating a toxicity dose-response profile for the patient based on the first and second side effect data.

83. The computer-implemented method of Example 82, wherein the first and second side effect data include data representing one or more of a type, a timing, a duration, a frequency, or a severity of at least one side effect experienced by the patient.

84. The computer-implemented method of Example 83, wherein the at least side effect comprises one or more of the following: drowsiness, a decrease in cognition, a decrease in attention, a decrease in concentration, a change in mood, a change in behavior, loss of consciousness, suicidality, homicidality, irritability, or a change in vision.

85. The computer-implemented method of any one of Examples 82 to 84, wherein the toxicity dose-response profile represents a change in side effect severity between the baseline time period and the treatment time period.

86. The computer-implemented method of any one of Examples 82 to 85, wherein:

the first seizure data is determined from a subset of the first eye movement data associated with an ictal period, the first side effect data is determined from a subset of the first eye movement data associated with an interictal period, the second seizure data is determined from a subset of the second eye movement data associated with an ictal period, the second side effect data is determined from a subset of the second eye movement data associated with an interictal period.

87 The computer-implemented method of any one of Examples 73 to 86, further comprising providing a treatment recommendation for the patient, based on the therapeutic dose-response profile.

88. A system for monitoring a patient having a neurological disease or condition, the system comprising:

one or more processors; and a memory operably coupled to the one or more processors and storing instructions that, when executed by the processor, cause the system to perform operations comprising:

receiving baseline eye movement data from an eye tracking device associated with the patient, determining, using the baseline eye movement data, first seizure data for the patient, receiving treatment eye movement data from the eye tracking device associated with the patient, determining, using the treatment eye movement data, second seizure data for the patient, and generating a therapeutic dose-response profile based on the first and second seizure data.

89. The system of Example 88, further comprising the eye tracking device.

90 The system of Example 89, wherein the eye tracking device is a wearable device.

91. The system of Example 89 or 90, wherein the eye tracking device is an electrooculography-based device.

92. The system of Example 89 or 90, wherein the eye tracking device is a video-based device.

93. The system of any one of Examples 88 to 92, wherein the eye tracking device is operably coupled to a computing device, and the baseline patient data and the treatment data are transmitted from the eye tracking device to the system via the computing device.

94. The system of any one of Examples 88 to 93, wherein the first and second eye movement data each include one or more of the following: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, eye rolling, jerky eye movements, saccadic velocity, saccadic direction, torsional velocity, torsional direction, gaze direction, gaze scanning patterns, or eye activity during sleep.

95. The system of any one of Examples 88 to 94, wherein the operations further comprise receiving additional data, wherein one or more of the first seizure data or the second seizure data are determined based on the additional data.

96. The system of Example 95, wherein the additional data is received from one or more of the following: a facial tracking device, a brain monitoring device, a mobile device, an implantable device, a wearable device, or a computing device.

97. The system of Example 95 or 96, wherein the additional data comprises one or more of the following: facial movement data, brain monitoring data, neuropsychological assessment data, self-reporting data, or electronic health record data.

98. The system of any one of Examples 88 to 97, wherein the first and second seizure data include data representing one or more of a type, a timing, an ictal duration, a postictal duration, a frequency, a severity, or a variability of at least one seizure event experienced by the patient.

99. The system of any one of Examples 88 to 98, wherein the therapeutic dose-response profile represents a change in seizure burden.

100. The system of any one of Examples 88 to 99, wherein the operations further comprise:

determining, using the baseline eye movement data, first side effect data for the patient, determining, using the treatment eye movement data, second side effect data for the patient, and generating a toxicity dose-response profile for the patient based on the first and second side effect data.

101. The system of Example 100, wherein the first and second side effect data include data representing one or more of a type, a timing, a duration, a frequency, or a severity of at least one side effect experienced by the patient.

102. The system of Example 101, wherein the at least side effect comprises one or more of the following: drowsiness, a decrease in cognition, a decrease in attention, a decrease in concentration, a change in mood, a change in behavior, loss of consciousness, suicidality, homicidality, irritability, or a change in vision.

103. The system of any one of Examples 100 to 102, wherein the toxicity dose-response profile represents a change in side effect severity between the baseline time period and the treatment time period.

104. The system of any one of Examples 88 to 103, wherein the operations further comprise providing a treatment recommendation for the patient, based on the therapeutic dose-response profile.

105. A non-transitory computer-readable storage medium comprising instructions that, when executed by one or more processors of a computing system, cause the computing system to perform operations comprising:

determining, based on baseline eye movement data produced by an eye tracking device associated with a patient, first seizure data during a baseline time period;

determining, based on treatment eye movement data produced by the eye tracking device associated with the patient, second seizure data during a treatment time period; and generating a therapeutic dose-response profile for the patient based on the first and second seizure data.

Conclusion

Although many of the embodiments are described above with respect to systems, devices, and methods for monitoring and managing epilepsy, the technology is applicable to other applications and/or other approaches, such as monitoring and managing other types of neurological diseases and conditions that are associated with loss of consciousness and/or lapses in cognitive function, as well as neurodegenerative diseases. Examples of such diseases and conditions include, but are not limited to, Tay-Sachs disease, ADHD, Parkinson's disease, syncope, and rare/orphan diseases such as tuberous sclerosis and Rett syndrome. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1A-9D.

The various processes described herein can be partially or fully implemented using program code including instructions executable by one or more processors of a computing system for implementing specific logical functions or steps in the process. The program code can be stored on any type of computer-readable medium, such as a storage device including a disk or hard drive. Computer-readable media containing code, or portions of code, can include any appropriate media known in the art, such as non-transitory computer-readable storage media. Computer-readable media can include volatile and non-volatile, removable and non-removable media implemented in any method or technology for storage and/or transmission of information, including, but not limited to, random-access memory (RAM), read-only memory (ROM), electrically erasable programmable read-only memory (EEPROM), flash memory, or other memory technology; compact disc read-only memory (CD-ROM), digital video disc (DVD), or other optical storage; magnetic cassettes, magnetic tape, magnetic disk storage, or other magnetic storage devices; solid state drives (SSD) or other solid state storage devices; or any other medium which can be used to store the desired information and which can be accessed by a system device.

The embodiments described above may be implemented in many different ways. In some embodiments, the various computing systems described herein may each be implemented by a separate or shared physical or virtual general-purpose computer having one or more central processor(s), memor(ies), disk or other mass storage device(s), communication interface(s), input/output (I/O) device(s), and other peripherals. The processors may operate, for example, by loading software instructions, and then executing the instructions to carry out the functions described. As is known in the art, such a computer may contain a system bus, where a bus is a set of hardware wired connections used for data transfer among the components of a computer or processing system. The bus or busses are shared conduit(s) that connect different elements of the computer system (e.g., processor, disk storage, volatile and non-volatile memory, input/output ports, network ports, etc.) to enable the transfer of information. One or more central processor units are attached to the system bus and provide for the execution of computer instructions. Also attached to the system bus are typically I/O device interfaces for connecting various input and output devices (e.g., keyboard, mouse, displays, printers, speakers, etc.) to the computer. Network interface(s) allow the computer to connect to various other devices attached to a network. Memory provides volatile or non-volatile storage for computer software instructions and data used to implement an embodiment. Disk or other mass storage provides non-volatile storage for computer software instructions and data used to implement, for example, the various procedures described herein.

Embodiments may therefore typically be implemented in hardware, firmware, software, or any combination thereof. In some embodiments, the computers that execute the processes described above are deployed in a cloud computing arrangement that makes available one or more physical and/or virtual data processing machines via a convenient, on-demand network access model to a shared pool of configurable computing resources (e.g., networks, servers, storage, applications, and services) that can be rapidly provisioned and released with minimal management effort or service provider interaction. Such cloud computing deployments can allow multiple users to access computing resources. By aggregating demand from multiple users in central locations, cloud computing environments can be built in data centers that use the best and newest technology, located in the sustainable and/or centralized locations and designed to achieve the greatest per-unit efficiency possible.

Furthermore, firmware, software, routines, or instructions may be described herein as performing certain actions and/or functions. It also should be understood that the block and network diagrams may include more or fewer elements, be arranged differently, or be represented differently. Therefore, it will be appreciated that such descriptions contained herein are merely for convenience and that such actions can result from computing devices, processors, controllers, or other devices executing the firmware, software, routines, instructions, etc.

Other modifications and variations are possible in light of the above teachings. For example, while a series of steps has been described above with respect to the flow diagrams, the order of the steps may be modified in other embodiments. In addition, the steps and operations may be performed by additional or other modules or entities, which may be combined or separated to form other modules or entities. For example, while a series of steps has been described with regard to certain figures, the order of the steps may be modified in other embodiments consistent with the principles of the present technology. Further, non-dependent steps may be performed in parallel. Further, disclosed embodiments may not be limited to any specific combination of hardware.

Certain portions may be implemented as "logic" that performs one or more functions. This logic may include hardware, such as hardwired logic, an application-specific integrated circuit, a field programmable gate array, a microprocessor, software, firmware, or a combination thereof. Some or all of the logic may be stored in one or more tangible non-transitory computer-readable storage media and may include computer-executable instructions that may be executed by a computer or data processing system. The computer-executable instructions may include instructions that implement one or more embodiments described herein. The tangible non-transitory computer-readable storage media may be volatile or non-volatile and may include, for example, flash memories, dynamic memories, removable disks, and non-removable disks.

Accordingly, further embodiments may also be implemented in a variety of computer architectures, physical, virtual, cloud computers, and/or some combination thereof, and thus the computer systems described herein are intended for purposes of illustration only and not as a limitation of the embodiments.

In practicing the subject methods, determining the presence or absence of a change in a signal may involve machine learning. Machine learning techniques and computational methods may be used for predicting seizures, syncope, drowsiness, loss of consciousness, and/or other neurological events or conditions from the data obtained. The machine learning process may involve relating the numerical data to the outcomes, which applies categorical training to detect and/or predict a condition or event. In some embodiments, machine learning models may include aspects of signal acquisition, signal pre-processing, features extraction from the signals, and classification between different seizure states. The disclosed methods and systems may also include confirming the presence or absence of a change relative to baseline, performing lower order statistical analysis and/or a higher order statistical analysis of the data.

Open-source tools may be employed to develop the methods described herein. This may include numerical processing languages such as Python or R, and deep learning development toolkits, such as TensorFlow, PyTorch, and Keras, to name a few. Commercially available tools such as MATLAB's Statistics and Machine Learning Toolbox™, Neural Network Toolbox™, Image Processing Toolbox™, the Image Acquisition Toolbox™, Mapping Toolbox™ and other MATLAB tools, such as the MATLAB Signal Processing Toolbox™ may also be leveraged to provide the machine learning and signal processing methods described herein.

No element, act, or instruction used herein should be construed as critical or essential to the disclosure unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

Also, the term "user," as used herein, is intended to be broadly interpreted to include, for example, a computer or data processing system or a human user of a computer or data processing system, unless otherwise stated.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms "generally," "substantially," "about," and similar terms are used as terms of approximation and not as terms of degree, and are intended to account for the inherent variations in measured or calculated values that would be recognized by those of ordinary skill in the art.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded.

To the extent any materials incorporated herein by reference conflict with the present disclosure, the present disclosure controls.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for monitoring a patient having a neurological disease or condition, the system comprising:

one or more processors; and a memory operably coupled to the one or more processors and storing instructions that, when executed by the one or more processors, cause the system to perform operations comprising:

receiving, from one or more patient monitoring devices configured to produce eye movement data, first patient data for a baseline time period before the patient has started taking a medication for the neurological disease or condition, determining, based on the first patient data, first seizure data and first side effect data during the baseline time period, receiving, from the one or more patient monitoring devices, second patient data for a treatment time period in which the patient is taking the medication, determining, based on the second patient data, second seizure data and second side effect data during the treatment time period, generating and outputting a visualization of a personalized dose-response profile for the patient, wherein the visualization of the personalized dose-response profile comprises: (1) a visual representation of a therapeutic profile representing a relationship between seizure control and different dosages of the medication determined based on the first and second seizure data, and (2) a visual representation of a toxicity profile representing a relationship between side effect severity and the different dosages of the medication determined based on the first and second side effect data, and outputting a treatment recommendation for the patient, wherein the treatment recommendation comprises administering a dosage of the medication to the patient to treat the neurological disease or condition, and wherein the dosage is selected based on the personalized dose-response profile.

2. The system of claim 1, wherein the neurological disease or condition comprises epilepsy or a disorder having epilepsy as a symptom.

3. The system of claim 1, wherein the one or more patient monitoring devices comprise an eye tracking device.

4. The system of claim 1, wherein the eye movement data includes one or more of the following: blink rate, blink duration, eye eccentricity, eye gaze angle, pupil size, pupil constriction amount, pupil constriction velocity, pupil dilation amount, pupil dilation velocity, pupil location, pupil rotation, pupil area to iris area ratio, hippus, eyelid movement rate, eyelid openings, eyelid closures, eyelid height, upward eyeball movements, downward eyeball movements, lateral eyeball movements, eye rolling, jerky eye movements, saccadic velocity, saccadic direction, torsional velocity, torsional direction, gaze direction, gaze scanning patterns, or eye activity during sleep.

5. The system of claim 1, wherein the one or more patient monitoring devices comprise one or more of the following: a facial tracking device, a brain monitoring device, a mobile device, an implantable device, a wearable device, or a computing device.

6. The system of claim 1, wherein the first and second seizure data include data representing one or more of a type, a timing, an ictal duration, a postictal duration, a frequency, a severity, or a variability of at least one seizure event experienced by the patient.

7. The system of claim 6, wherein the at least one seizure event comprises one or more of the following: an absence seizure, an atypical absence seizure, a tonic-clonic seizure, a clonic seizure, a tonic seizure, an atonic seizure, a myoclonic seizure, a simple partial seizure, a complex partial seizure, a secondary generalized seizure, or an infantile spasm.

8. The system of claim 1, wherein the operations further comprise comparing the first and second seizure data to determine a change in seizure burden between the baseline time period and the treatment time period.

9. The system of claim 1, wherein the first and second side effect data include data representing one or more of a type, a timing, a duration, a frequency, or a severity of at least one side effect experienced by the patient.

10. The system of claim 9, wherein the at least one side effect comprises one or more of the following: drowsiness, a decrease in cognition, a decrease in attention, a decrease in concentration, a change in mood, a change in behavior, a change in memory, loss of consciousness, suicidality, homicidality, irritability, or a change in vision.

11. The system of claim 1, wherein the operations further comprise comparing the first and second side effect data to determine a change in side effect severity between the baseline time period and the treatment time period.

12. A system for managing epilepsy, the system comprising:

one or more processors; and a memory operably coupled to the one or more processors and storing instructions that, when executed by the one or more processors, cause the system to perform operations comprising:

receiving, from an eye tracking device, first eye movement data of a patient during a baseline period before the patient has started taking a medication for the epilepsy, determining, based on the first eye movement data, first seizure burden data and first neurocognitive data for the patient during the baseline period, receiving, from the eye tracking device, second eye movement data of the patient during a treatment period in which the patient is taking the medication, determining, based on the second eye movement data, second seizure burden data and second neurocognitive data for the patient during the treatment period, generating and outputting a visualization of a personalized dose-response profile for the patient, wherein the visualization of the personalized dose-response profile comprises: (1) a visual representation of a therapeutic profile representing a relationship between seizure control and different dosages of the medication determined based on the first and second seizure burden data, and (2) a visual representation of a toxicity profile representing a relationship between neurocognitive state and the different dosages of the medication determined based on the first and second neurocognitive data, and outputting a treatment recommendation for the patient, wherein the treatment recommendation comprises administering a dosage of the medication to the patient to treat the epilepsy, and wherein the dosage is selected based on the personalized dose-response profile.

13. The system of claim 12, wherein:

the first and second seizure burden data are determined from the first and second eye movement data using a first set of algorithms, and the first and second neurocognitive data are determined from the first and second eye movement data using a second set of algorithms.

14. The system of claim 13, wherein the first set of algorithms includes at least one machine learning algorithm trained on seizure data from a plurality of patients, and the second set of algorithms includes at least one machine learning algorithm trained on interictal data from a plurality of patients.

15. The system of claim 12, wherein the operations further comprise:

receiving, from the eye tracking device, third eye movement data for a subsequent treatment period during which the patient is taking a different dosage of the medication, and determining, based on the third eye movement data, third seizure burden data and third neurocognitive data during the subsequent treatment period, wherein the personalized dose-response profile for the patient is generated based on the third seizure burden data and the third neurocognitive data.

16. The system of claim 12, wherein the operations further comprise receiving additional patient data, wherein one or more of the first seizure burden data, first neurocognitive data, second seizure burden data, or second neurocognitive data are determined based on the additional patient data, and wherein the additional patient data is received from one or more of the following: a facial tracking device, a brain monitoring device, a mobile device, an implantable device, a wearable device, or a computing device.

17. The system of claim 12, wherein the treatment recommendation is determined using a machine learning algorithm trained on dose-response profiles from a plurality of patients.

18. The system of claim 12, wherein the first and second neurocognitive data include data representing one or more of a type, a timing, a duration, a frequency, or a severity of at least one change to the patient's attention, mood, or memory.

19. The system of claim 12, wherein the eye tracking device comprises a camera of a mobile device.

20. The system of claim 12, wherein the visualization of the personalized dose-response profile further comprises a visual representation of a natural history curve indicating changes to the patient's baseline neurocognitive state.

* * * * *